United States Patent
Nolte et al.

(10) Patent No.: US 7,522,282 B2
(45) Date of Patent: Apr. 21, 2009

(54) MOLECULAR INTERFEROMETRIC IMAGING PROCESS AND APPARATUS

(75) Inventors: David D. Nolte, Lafayette, IN (US); Ming Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 81 days.

(21) Appl. No.: 11/744,726

(22) Filed: May 4, 2007

(65) Prior Publication Data

US 2008/0129981 A1 Jun. 5, 2008

Related U.S. Application Data

(60) Provisional application No. 60/867,961, filed on Nov. 30, 2006.

(51) Int. Cl.
*G01B 9/02* (2006.01)
(52) U.S. Cl. ..................................... 356/450
(58) Field of Classification Search .............. 356/450, 356/451, 456
See application file for complete search history.

(56) References Cited

U.S. PATENT DOCUMENTS

| | | |
|---|---|---|
| 3,796,495 A | 3/1974 | Laub |
| 4,537,861 A | 8/1985 | Elings et al. |
| 4,741,620 A | 5/1988 | Wickramasinghe |
| 4,876,208 A | 10/1989 | Gustafson et al. |
| 4,899,195 A | 2/1990 | Gotoh |
| 4,975,237 A | 12/1990 | Watling |
| RE33,581 E | 4/1991 | Nicoli et al. |
| 5,122,284 A | 6/1992 | Braynin et al. |
| 5,155,549 A | 10/1992 | Dhadwal |
| 5,413,939 A | 5/1995 | Gustafson et al. |
| 5,478,527 A | 12/1995 | Gustafson et al. |
| 5,478,750 A | 12/1995 | Bernstein et al. |

(Continued)

FOREIGN PATENT DOCUMENTS

EP 1189062 A1 3/2002

(Continued)

OTHER PUBLICATIONS

P. B. Luppa, L. J. Sokoll, and D. W. Chan, "Immunosensors—principles and applications to clinical chemistry," *Clinica Chimica Acta*, vol. 314, pp. 1-26, 2001.

(Continued)

*Primary Examiner*—Hwa (Andrew) S Lee
(74) *Attorney, Agent, or Firm*—Bose McKinney & Evans LLP

(57) ABSTRACT

A molecular interferometric imaging system for detecting an analyte in a sample, that includes an illumination source providing a beam of radiation; a pixel array for detecting radiation in an image plane; a biolayer designed to react to the analyte when it comes in contact with the sample; a substrate designed to convert phase modulation into intensity modulation which can be detected and imaged directly by the pixel array, the biolayer being on the substrate; a reference surface; an image switching means for switching between a first position for collecting a sample image of the biolayer, and a second position for collecting a reference image of the reference surface; and a processing means for producing a composite image using the sample image and the reference image for illumination normalization.

34 Claims, 10 Drawing Sheets

U.S. PATENT DOCUMENTS

| | | |
|---|---|---|
| 5,494,829 A | 2/1996 | Sandstrom et al. |
| 5,497,007 A | 3/1996 | Uritsky et al. |
| 5,545,531 A | 8/1996 | Rava et al. |
| 5,581,345 A | 12/1996 | Oki et al. |
| 5,602,377 A | 2/1997 | Beller et al. |
| 5,621,532 A | 4/1997 | Ooki et al. |
| 5,629,044 A | 5/1997 | Rubenchik |
| 5,631,171 A | 5/1997 | Sandstrom et al. |
| 5,653,939 A | 8/1997 | Hollis et al. |
| 5,700,046 A | 12/1997 | Van Doren et al. |
| 5,717,778 A | 2/1998 | Chu et al. |
| 5,736,257 A | 4/1998 | Conrad et al. |
| 5,781,649 A | 7/1998 | Brezoczky |
| 5,786,226 A | 7/1998 | Bocker et al. |
| 5,837,475 A | 11/1998 | Dorsel et al. |
| 5,843,767 A | 12/1998 | Beattie |
| 5,844,871 A | 12/1998 | Maezawa |
| 5,874,219 A | 2/1999 | Rava et al. |
| 5,875,029 A | 2/1999 | Jann et al. |
| 5,892,577 A | 4/1999 | Gordon |
| 5,900,935 A | 5/1999 | Klein et al. |
| 5,922,617 A | 7/1999 | Wang et al. |
| 5,935,785 A | 8/1999 | Reber et al. |
| 5,945,344 A | 8/1999 | Hayes et al. |
| 5,955,377 A | 9/1999 | Maul et al. |
| 5,968,728 A | 10/1999 | Perttunen et al. |
| 5,999,262 A | 12/1999 | Dobschal et al. |
| 6,008,892 A | 12/1999 | Kain et al. |
| 6,030,581 A | 2/2000 | Virtanen |
| 6,048,692 A | 4/2000 | Maracas et al. |
| 6,060,237 A | 5/2000 | Nygren et al. |
| 6,071,748 A | 6/2000 | Modlin et al. |
| 6,099,803 A | 8/2000 | Ackley |
| 6,110,748 A | 8/2000 | Reber et al. |
| 6,121,048 A | 9/2000 | Zaffaroni et al. |
| 6,140,044 A | 10/2000 | Besemer et al. |
| 6,143,247 A | 11/2000 | Sheppard, Jr. et al. |
| 6,177,990 B1 | 1/2001 | Kain et al. |
| 6,221,579 B1 | 4/2001 | Everhart et al. |
| 6,238,869 B1 | 5/2001 | Kris et al. |
| 6,248,539 B1 | 6/2001 | Ghadiri et al. |
| 6,249,593 B1 | 6/2001 | Chu et al. |
| 6,256,088 B1 | 7/2001 | Gordon |
| 6,271,924 B1 | 8/2001 | Ngoi et al. |
| 6,287,783 B1 | 9/2001 | Maynard et al. |
| 6,287,850 B1 | 9/2001 | Besemer et al. |
| 6,312,901 B2 | 11/2001 | Virtanen |
| 6,312,961 B1 | 11/2001 | Voirin et al. |
| 6,319,468 B1 | 11/2001 | Sheppard, Jr. et al. |
| 6,319,469 B1 | 11/2001 | Mian et al. |
| 6,320,665 B1 | 11/2001 | Ngoi et al. |
| 6,327,031 B1 | 12/2001 | Gordon |
| 6,339,473 B1 | 1/2002 | Gordon |
| 6,342,349 B1 | 1/2002 | Virtanen |
| 6,342,395 B1 | 1/2002 | Hammock et al. |
| 6,345,115 B1 | 2/2002 | Ramm et al. |
| 6,350,413 B1 | 2/2002 | Reichert et al. |
| 6,355,429 B1 | 3/2002 | Nygren et al. |
| 6,368,795 B1 | 4/2002 | Hefti |
| 6,376,258 B2 | 4/2002 | Hefti |
| 6,381,025 B1 | 4/2002 | Bornhop et al. |
| 6,387,331 B1 | 5/2002 | Hunter |
| 6,395,558 B1 | 5/2002 | Duveneck et al. |
| 6,395,562 B1 | 5/2002 | Hammock et al. |
| 6,399,365 B2 | 6/2002 | Besemer et al. |
| 6,403,957 B1 | 6/2002 | Foder et al. |
| 6,416,642 B1 | 7/2002 | Alajoki et al. |
| 6,469,787 B1 | 10/2002 | Meyer et al. |
| 6,476,907 B1 | 11/2002 | Gordon |
| 6,483,585 B1 | 11/2002 | Yang |
| 6,483,588 B1 | 11/2002 | Graefe et al. |
| 6,496,309 B1 | 12/2002 | Bliton et al. |
| 6,504,618 B2 | 1/2003 | Morath et al. |
| 6,518,056 B2 | 2/2003 | Schembri et al. |
| 6,551,817 B2 | 4/2003 | Besemer et al. |
| 6,566,069 B2 | 5/2003 | Virtanen |
| 6,584,217 B1 | 6/2003 | Lawless et al. |
| 6,591,196 B1 | 7/2003 | Yakhini et al. |
| 6,596,483 B1 | 7/2003 | Choong et al. |
| 6,602,702 B1 | 8/2003 | McDevitt et al. |
| 6,623,696 B1 | 9/2003 | Kim et al. |
| 6,624,896 B1 | 9/2003 | Neal et al. |
| 6,649,403 B1 | 11/2003 | McDevitt et al. |
| 6,653,152 B2 | 11/2003 | Challener |
| 6,656,428 B1 | 12/2003 | Clark et al. |
| 6,685,885 B2 | 2/2004 | Nolte et al. |
| 6,687,008 B1 | 2/2004 | Peale et al. |
| 6,709,869 B2 | 3/2004 | Mian et al. |
| 6,720,177 B2 | 4/2004 | Ghadiri et al. |
| 6,733,977 B2 | 5/2004 | Besemer et al. |
| 6,734,000 B2 | 5/2004 | Bhatia |
| 6,737,238 B2 | 5/2004 | Suzuki et al. |
| 6,743,633 B1 | 6/2004 | Hunter |
| 6,760,298 B2 | 7/2004 | Worthington et al. |
| 6,766,817 B2 | 7/2004 | da Silva |
| 6,770,447 B2 | 8/2004 | Maynard et al. |
| 6,783,938 B2 | 8/2004 | Nygren et al. |
| 6,787,110 B2 | 9/2004 | Tiefenthaler |
| 6,791,677 B2 | 9/2004 | Kawai et al. |
| 6,803,999 B1 | 10/2004 | Gordon |
| 6,806,963 B1 | 10/2004 | Walti et al. |
| 6,819,432 B2 | 11/2004 | Pepper et al. |
| 6,836,338 B2 | 12/2004 | Opsal et al. |
| 6,844,965 B1 | 1/2005 | Engelhardt |
| 6,847,452 B2 | 1/2005 | Hill |
| 6,878,555 B2 | 4/2005 | Anderson et al. |
| 6,897,965 B2 | 5/2005 | Ghadiri et al. |
| 6,917,421 B1 | 7/2005 | Wihl et al. |
| 6,917,432 B2 | 7/2005 | Hill et al. |
| 6,918,404 B2 | 7/2005 | da Silva |
| 6,937,323 B2 | 8/2005 | Worthington et al. |
| 6,955,878 B2 | 10/2005 | Kamabara et al. |
| 6,958,131 B2 | 10/2005 | Tiefenthaler |
| 6,980,299 B1 | 12/2005 | De Boer |
| 6,980,677 B2 | 12/2005 | Niles et al. |
| 6,987,569 B2 | 1/2006 | Hill |
| 6,990,221 B2 | 1/2006 | Shams |
| 6,992,769 B2 | 1/2006 | Gordon |
| 6,995,845 B2 | 2/2006 | Worthington |
| 7,006,927 B2 | 2/2006 | Yakhini et al. |
| 7,008,794 B2 | 3/2006 | Goh et al. |
| 7,012,249 B2 | 3/2006 | Krutchinsky et al. |
| 7,014,815 B1 | 3/2006 | Worthington et al. |
| 7,026,131 B2 | 4/2006 | Hurt et al. |
| 7,027,163 B2 | 4/2006 | Angeley |
| 7,031,508 B2 | 4/2006 | Lawless et al. |
| 7,033,747 B2 | 4/2006 | Gordon |
| 7,042,570 B2 | 5/2006 | Sailor |
| 7,061,594 B2 | 6/2006 | Worthington et al. |
| 7,066,586 B2 | 6/2006 | Da Silva |
| 7,070,987 B2 | 7/2006 | Cunningham et al. |
| 7,077,996 B2 | 7/2006 | Randall et al. |
| 7,083,920 B2 | 8/2006 | Werner et al. |
| 7,087,203 B2 | 8/2006 | Gordon et al. |
| 7,088,650 B1 | 8/2006 | Worthington et al. |
| 7,091,034 B2 | 8/2006 | Virtanen |
| 7,091,049 B2 | 8/2006 | Boga et al. |
| 7,094,595 B2 | 8/2006 | Cunningham et al. |
| 7,094,609 B2 | 8/2006 | Demers |
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |

| | | |
|---|---|---|
| 7,118,855 B2 | 10/2006 | Cohen et al. |
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | De Boer |
| 7,200,088 B2 | 4/2007 | Worthington et al. |
| 7,221,632 B2 | 5/2007 | Worthington |
| 7,345,770 B2 * | 3/2008 | Chan et al. .................. 356/489 |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1 | 5/2002 | Demers |
| 2002/0085202 A1 | 7/2002 | Gordon |
| 2002/0097658 A1 | 7/2002 | Worthington et al. |
| 2002/0106661 A1 | 8/2002 | Virtanen |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0078337 A1 | 4/2004 | King et al. |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1 | 8/2004 | Sorin |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1 | 11/2005 | Tan et al. |
| 2005/0259260 A1 | 11/2005 | Wakita |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256350 A1 | 11/2006 | Nolte et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003925 A1 | 1/2007 | Nolte et al. |
| 2007/0003979 A1 | 1/2007 | Worthington |
| 2007/0023643 A1 | 2/2007 | Nolte et al. |
| 2007/0070848 A1 | 3/2007 | Worthington et al. |
| 2007/0077599 A1 | 4/2007 | Krutzik |
| 2007/0077605 A1 | 4/2007 | Hurt et al. |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 8/1998 |
| WO | WO 0000265 | 1/2000 |
| WO | WO 0039584 | 7/2000 |
| WO | WO 0111310 | 2/2001 |
| WO | WO 0144441 | 6/2001 |
| WO | WO 06042746 | 4/2006 |

OTHER PUBLICATIONS

C. L. Tucker, J. F. Gera, and P. Uetz, "Towards an understanding of complex protein networks," *Trends In Cell Biology*, vol. 11, pp. 102-106, 2001.

P. Uetz and R. L. Finley, "From protein networks to biological systems," *Febs Letters*, vol. 579, pp. 1821-1827, 2005.

G. Gauglitz, "Direct optical sensors: principles and selected applications," Analytical And Bioanalytical Chemistry, vol. 381, pp. 141-155, 2005.

M. Zhao, D. D. Nolte, W. R. Cho, F. Regnier, M. Varma, G. Lawrence, and J. Pasqua, "High-speed interferometric detection of label-free immunoassays on the biological compact disc," *J. Clin. Chem.*, vol. 52, pp. 2135-2140, 2006.

David D. Nolte and Ming Zhao, "*Scaling mass sensitivity of the BioCD at 0.25 pg/mm*," Proc. SPIE Int. Soc. Opt. Eng. 6380, 63800J (2006), DOI:10.1117/12.686307 (6 pages).

H. Ozen and S. Sozen, "PSA Isoforms in prostate cancer detection," *Eur. Urol. Suppl.*, vol. 5, pp. 495-499, 2006.

S. P. Balk, Y.-J. Ko, and G. J. Bubley, "Biology of Prostate-specific antigen," J. Clin. Onc., vol. 21, pp. 383-391, 2003.

Wang, M.C., Papsidero, L.D., Kuriyama, M., Valenzuela, G.P. and Chu, T.M. 1981. Prostate antigen: A new potential marker for prostatic cancer. *The Prostate* 2: 89-96.

Lovgren J, Valtonen-Andre C, Marsal K, et al: Measurement of prostate-specific antigen and human glandular kallikrein 2 in different body fluids. J. Androl. 20:348-355, 1999.

J. Homola, "Present and future of surface plasmon resonance biosensors," Analytical And Bioanalytical Chemistry, vol. 377, pp. 528-539, 2003.

Xia, Y., et al. Non Photolithographic Methods and Fabrication of Elastomeric Stamps for Use in Microcontact Printing, Langmuir, 1996, vol. 12, pp. 4033-4038.

Hu, J., et al. Using Soft Lithography to Fabricate GaAs/AlGaAs Heterostructure Field Effect Transistors, Appl. Phys. Lett., 1997 vol. 71, pp. 2020-2002.

Grzybowski, B.A., et al. Generation of Micrometer-Sized Patterns for Microanalytical Applications Using a Laser Direct-Write Method and Microcontact Printing, Anal. Chem., 1998, vol. 70, pp. 4645-4652.

Martin, B.D., et al. Direct Protein Microarray Fabrication Using a Hydrogel Stamper, Langmuir, 1998, vol. 14, pp. 3971-1975.

Pompe, T., et al. Submicron Contact Printing on Silicon Using Stamp Pads, Langmuir, 1999, vol. 15, pp. 2398-2401.

Bietsch, A. and B. Michel. Conformal Contact and Pattern Stability of Stamps Used for Soft Lithography, J. Appl. Phys., 2000, vol. 88, pp. 4310-4318.

Geissler, M., et al. Microcontact Printing Chemical Patterns with Flat Stampes, J. Am. Chem. Soc., 2000, vol. 122, pp. 6303-6304.

Sanders, G.H.W. and A. Manz. Chip-based Microsystems for Genomic and Proteomic Analysis. Trends in Anal. Chem., 2000, vol. 19(6), pp. 364-378.

Wang, J. Survey and Summary from DNA Biosensors to Gene Chips, Nucl. Acids Res., 2000, vol. 28(16), pp. 3011-3016.

Hagman, M. Doing Immunology on a Chip, Science, vol. 290, pp. 82-83.

Marx, J. DNA Arrays Reveal Cancer in its Many Forms, Science, 2000, vol. 289, pp. 1670-1672.

Effenhauser, C.S., et al. Integrated Capillary Electrophoresis on Flexible Silicon Microdevices: Analysis of DNA Restriction Fragments and Detection of Single DNA Molecules on Microchips, Anal. Chem., 1997, vol. 69, pp. 3451-3457.

He, B. and F.E. Regnier, Fabrication of Nanocolumns for Liquid Chromatography, Anal. Chem., 1998, vol. 70, p. 3790-3797.

Kricka, L.J. Miniaturization of Analytical Systems, Clin. Chem., 1998, vol. 44(9), pp. 2008-2014.

Regnier, F.E., et al. Chromatography and Electrophoresis on Chips: Critical Elements of Future Integrated Microfluidic Analytical Systems for Life Science, Tibtech, 1999, vol. 17, pp. 101-106.

Ekins, R., F. Chu, and E. Biggart, Development of Microspot Multi-Analyte Ratiometric Immunoassay Using Dual Flourescent-Labelled Antibodies, Anal. Chim. Acta, 1989, vol. 227, pp. 73-96.

Ekins, R. et al. Multianalyte Microspot Immunoassay. The Microanalytical Compact Disk of the Future: Clin. Chem., 1991, vol. 37(11), pp. 1955-1967.

Ekins, R., Ligand Assays: From Electrophoresis to Miniaturized microarrays, Clin. Chem., 1998, vol. 44(9), pp. 2015-2030.

Gao, H., et al. Immunosensing with Photo-Immobilized Immunoreagents on Planar Optical Wave Guides. Biosensors and Bioelectronics, 1995, vol. 10, pp. 317-328.

Maisenholder, B., et al. A GaAs/AlGaAs-based Refractometer Platform for Integrated Optical Sensing Applications. Sensors and Actuators B, 1997, vol. 38-39, pp. 324-329.

Kunz, R.E., Miniature Integrated Optical Modules for Chemical and Biochemical Sensing. Sensors and Actuators B, 1997, vol. 38-39, pp. 13-28.

Dübendorfer, J. and R.E. Kunz, Reference Pads for Miniature Integrated Optical Sensors. Sensors and Actuators B, 1997, vol. 38-39, pp. 116-121.

Brecht, A. and G. Gauglitz, Recent Developments in Optical Transducers for Chemical or Biochemical Applications, Sensors and Actuators B, 1997, vol. 38-39, pp. 1-7.

Scruby, C.B. and L.E. Drain, Laser Ultrasonics: Techniques and Applications. 1990, Bristol: Adam Hilger. pp. 116-123.

Nolte, D.D., et al. Adaptive Beam Combining and Interferometry Using Photorefractive Quantum Wells, J. Opt. Soc. Am. B, vol. 19, No. 2, Feb. 2001, pp. 195-205.

St. John, P. M., et al. Diffraction-Based Cell Detection Using a Microcontact Printed Antibody Grating, Anal. Chem., 1998, vol. 70(6), pp. 1108-1111.

Morhard, F., et al. Immobilization of Antibodies in Micropatterns for Cell Detection by Optical Diffraction. Sensors and Actuators B, vol. 70, pp. 232-242.

Rossomakhin, I., and S. Stepanov. Linear Adaptive Interferometers via Diffusion Recording in Cubic Photorefractive Crystals, Opt. Commun. vol. 86, 199-204 (1991).

Ing, R.K. and L.P. Monchalin, Broadband Optical Detection of Ultrasound by Two-Wave Mixing in a Photorefractive Crystal, Appl. Phys. Lett. 59, pp. 3233-3235 (1991).

Blouin, A., et al. Detection of Ultrasonic Motion of a Scattering Surface by Two-Wave Mixing in a Photorefractive GaAs Crystal, Appl. Phys. Lett., vol. 65, pp. 932-934 (1994).

Pouet, B.F., et al. Heterodyne Interferometer with Two-Wave Mixing in Photorefractive Crystals for Ultrasound Detection on Rough Surface, Appl. Phys. Lett., vol. 69, pp. 3782-3784 (1996).

Montmorillon, L.A., et al. Eye Safe Large Field of View Homodyne Detection Using a Photorefractive CdTe: V Crystal, Opt. Commun. vol. 29, pp. 293-300 (1996).

Delaye, P., et al., Detection of Ultrasonic Motion of a Scattering Surface by Photorefractive InP:Fe Under an Applied DC Field, J. Opt. Soc. Am. B, vol. 14, pp. 1723-1734 (1997).

Lahiri, I., et al. Laser-Based Ultrasound Detection Using Photorefractive Quantum Wells, Appl. Phys. Lett., vol. 73, pp. 1041-1043 (1998).

Balassubramanian, S., et al. Two-Wave Mixing Dynamics and Nonlinear Hot-Electron Transport in Transverse-Geometry Photorefractive Quantum Wells Studies by Moving Gratings, Appl. Phys. B., vol. 68, pp. 863-869 (1990).

Delamarche, E., et al. Patterned Delivery of Immunoglobulins to Surface Using Microfluidic Networks, Science, vol. 276, pp. 779-781 (1997).

Delamarche, E., et al. Microfluidic Networks for Chemical Patterning of Substrates: Design and Application to Bioassays, J. Am. Chem. Soc., vol. 120, pp. 500-508 (1998).

Kapur, R., et al. Streamlining the Drug Discovery Process by Integrating Miniaturization High Throughput Screening, High Content Screening, and Automation on the CellChipTM System. Biomedical Microdevices, vol. 1(2), 1999, pp. 99-109.

Jenison, R., et al. Interference-Based Detection of Nucleic Acid Targets on Optically Coated Silicon. Nat. Biotechnol. 19, pp. 62-65.

Fattinger, C., et al. The Difference Interferometer—A High Sensitive Optical Probe for Quantification of Molecular-Surface Concentration; Biosensors and Bioelectronics, vol. 8(2), pp. 99-107 (1993).

Jenison, R., et al. Silicon-Based Biosensors for Rapid Detection of Protein or Nucleic Acid Targets, Clin. Chem., vol. 47:10, pp. 1894-1900 (2001).

Varma, M.M., et al. High Speed Label Free Detection by Spinning-Disk Micro-Interferometry, Biosensors and Bioelectronics, vol. 19, pp. 1371-1376 (2004).

Varma, M.M., et al. Spinning-Disk Self-Referencing Interferometry of Antigen-Antibody Recognition, Opt. Letts., vol. 29, pp. 950-952 (2004).

Nolte, D.D., Semi-Insulating Semiconductor Heterostructures: Optoelectronic Properties and Applications, J. Appl. Phys., vol. 85, pp. 6259-6289 (1999).

Varma, M.M., et al. High-Speed Label-Free Multi-Analyte Detection through Micro-Interferometry, Proc. of SPIE, vol. 496, pp. 58-64 (2003).

Somekh, M., et al. Scanning Heterodyne Confocal Differential Phase and Intensity Microscope, Applied Optics, vol. 34(22), pp. 4857-4868 (1995).

Suddendorf, M., et al. Single-Probe-Beam Differential Amplitude and Phase-Scanning Interferometer, vol. 36:25, pp. 6202-6210 (1997).

See, C.W., et al. Scanning Differential Optical Profilometer for Simultaneous Measurement of Amplitude and Phase Variation, Appl. Phy. Lett., vol. 53:1, pp. 10-12 (1988).

Abe, T., et al. Microroughness Measurements on Polished Silicon Wafers, Jpn. J. Appl. Phys., vol. 31, pp. 721-728 (1992).

Nolte, D.D., et al. Spinning-Disk Interferometry: The BioCD, Optics & Photonics News, vol. 15:10, pp. 48-53 (2004).

Ding, Y., et al. Femtosecond Pulse Shaping by Dyanmic Holograms in Photorefractive Multiple Quantum Wells, Opt. Soc. Of Am., vol. 22:10, pp. 718-720 (1997).

Ding, Y., et al. Adaptive All-Order Dispersion Compensation of Ultrafast Laser Pulses Using Dynamic Spectral Holography, Appl. Phys. Letts., vol. 75(21), pp. 3255-3257 (1999).

Jones, R., et al. Adaptive Femtosecond Optical Pulse Combining, App. Phys. Letts., vol. 77(23), pp. 3692-3694 (2000).

Lahiri, I., et al. Photorefractive p-i-n Diode Quantum Well Spatial Light Modulators, Appl. Phys. Letts., vol. 67(10), pp. 1408-1410 (1995).

Nolte, D.D. Self-Adaptive Optical Holography in Quantum Wells, Pro. Of SPIE, vol. 3729, pp. 237-243, 1999.

Laclair, J., et al. Molecular Screening on a Compact Disc; The Royal Society of Chemistry, pp. 3244-3249 (2003).

Burkart, et al. UCSD Scientists Develop Novel Way to Screen Molecules Using Conventional CDS and Compact Disc Players; UCSD Newsletter, pp. 1-3, 2003.

Kwolek, K.M., et al. Photorefractive Asymmetric Fabry-Perot Quantum Wells: Transverse-filed Geometry, Appl. Phys. Letts., vol. 67, pp. 736-738 (1995).

Nolte, D., et al. Photorefractive Quantum Wells (Nov. 2004).

Peng, L., et al. Adaptive Optical Biocompact Disc for Molecular Recognition, Appl. Phys. Letts., vol. 86, 183902 (2005).

Gruska, B., et al. Fast and Reliable Thickness and Refractive Index Measurement of Antireflection Coatings on Solar-Silicon by Ellipsometery, Sentech Instruments GmbH, CarlOScheele-Str. 16, 12489 Berlin Germany.

Hecht, "Chapter 9.3: Wavefront-Splitting Interferometers," Optics, 1974, Addison-Wesley Publishing Co., Inc., pp. 281-286.

Nagarajan, R., Intensity-based segmentation of microarrays images, IEEE Trans. Med. Imaging, v22, 882-889 (2003).

Faramarzpour, N., Shirani, S. and Bondy, J., Lossless DNA microarray image compression, IEEE Conf. Signal Systems Comput. v2, 1501-1504 (2003).

Katzer, M., Kummert, F. and Sagerer, G., Methods for automatic microarray image segmentation, IEEE Trans. NanoBiosci. v2 i4, 202-214 (2003).

N. Brändle, H. Bischof, H. Lapp: *"Robust DNA Microarray Image Analysis"*; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Fabri, R: "Towards non-parametric gridding of Microarray images," *Digital Signal Processing, 2002, DSP 2002, 2002 14th International Conference publication*, vol.: 2, pp.: 623-626.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

MacBeath, G. and S. L. Schreiber, 2000, "Printing proteins as microarrays for high-throughput function determination." Science 289:1760-1763.

Guemouri, L., J. Ogier, and J. J. Ramsden, "Optical properties of protein monolayers during assembly," Journal of Chemical Physics 1998, 109:3265-3268.

Ostroff, R., A. Ettinger, H. LA, M. Rihanek, L. Zalman, J. Meador III, A. K. Patrick, S. Worland, and B. Polisky, 2001, "Rapid multiserotype detection of human rhinoviruses on optically coated silicon surfaces," J. Clin. Virol. 21: 105-117.

Jenison, R., Yang, S., Haeberli, A., and Polisky, B., "Interference-Based Detection of Nucleic Acid Targets on Optically Coated Silicon," Nature Biotechnology 19:62-65 (2001).

N. B. Sheller, S. Petrash, M. D. Foster, "Atomic Force Microscopy and X-ray Reflectivity Studies of Albumin Adsorbed onto Self-Assembled Monolayers of Hexadecyltrichlorosilane," *Langmuir*, 14, 4535-4544, 1998.

M. Varma, D. D. Nolte, H. D. Inerowicz, and F. E. Regnier, "Multi-Analyte Array Micro-Diffraction Interferometry," in *Microarrays: Design, Febrication and Reading*, vol. 4626, B. J. B. et al., Ed.: SPIE, 2002, pp. 69-77.

D. D. Nolte and M. R. Melloch, "Photorefractive Quantum Wells and Thin Films," in *Photorefractive Effects and Materials*, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric Fabry-Perot Reflection Modulator with very High Contrast Ratio," *IEEE Phot. Tech. Lett.*, vol. 5, pp. 55-58, 1993.

M. Whitehead and G. Parry, "High-contrast reflection modulation at normal incidence in asymmetric multiple quantum well Fabry-Perot structure," *Electron, Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated optical Mach-Zehnder interferometers as simazine immunoprobes," *Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Heller, "Microelectronic array devices and techniques for electric field enhanced DNA hybridization in low-conductance buffers," *Electrophoresis*, vol. 23, pp. 1543-1550, 2002.

Y. Joon Mo, J. Bell, H. Ying, M. Tirado, D. Thomas, A. H. Forster, R. W. Haigis, P. D. Swanson, R. B. Wallace, B. Martinsons, and M. Krihak, "An integrated stacked microlaboratory for biological agent detection with DNA and immunoassays," *Biosensors & Bioelectronics*, vol. 17, pp. 605-618, 2002.

M. J. Heller, "An active microelectronics device for multiplex DNA analysis," *IEEE Engineering in Medicine & Biology Magazine*, vol. 15, pp. 100-104, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal Fabry-Perot electrooptic modulators," *IEEE " Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," *Appl. Phys. Lett*, vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

Kwolek, K. M. et al., "Photorefractive Asymmetric Fabry-Perot Quantum Wells: Transverse-filed Geometry," Appl. Phys. Lett, vol. 67, pp. 736-738, 1995.

B. A. Grzybowski, R. Haag, N. Bowden, and G. M. Whitesides, "Generation of micrometersized patterns for microanalytical applications using a laser direct-write method and microcontact printing," *Anal. Chem.*, vol. 70, pp. 4645-4652, 1998.

T. Cass and F. S. Ligler, "Immobilized Biomolecules in Analysis: A Practical Approach Series vol. 98," Oxford: Oxford, 1998.; Chapter 2: Avidin-biotin immobilization systems, pp. 15-34.

R. Guersen, I. Lahiri, M. R. Melloch, J. M. Woodall and D. D. Nolte, Transient Enhanced Intermixing of Arsenic-Rich Nonstoichiometric AlAs/GaAs Quantum Wells, Phys. Rev. B60, 10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. McKenna, D. D. Nolte, W. Walukiewicz, and P. Becla, "Persistent holographic absorption gratings in AlSb:Se," *Appl. Phys. Lett.*, vol. 68, pp. 735-737, 1996.

R. S. Rana, E. Oh, K. Chua, A. K. Ramdas, and D. D. Nolte, "Voigtphotorefractive two-wave mixing in CdMnTe," *J. Lumin.*, vol. 60&61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effective-mass AlGaAs/GaAs Fibonacci superlattices," *Phys. Rev. B*, vol. 56, pp. 1987-1995, 1997.

M. Dinu, K. Nakagawa, M. R. Melloch, A. M. Weiner, and D. D. Nolte, "Broadband Low-Dispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwdith Study of Volume Holography in Photorefractive InP:Fe at 1.5 microns for Frequency Domain Femtosecond Pulse Processing," *J. Opt. Soc. B*, vol. 15, pp. 2763-2768, 1998.

Y. Ding, I. Lahiri, D. D. Nolte, G. J. Dunning, and D. M. Pepper, "Electric Field Correlation of Femtosecond Pulses using a Photo-Electromotive Force Detector," *J. Opt. Soc. Am. B*, vol. 15, pp. 2013-2017, 1998.

R. Jones, N. P. Barry, S. C. W. Hyde, P. M. W. French, K. M. Kwolek, D. D. Nolte, and M. R. Melloch, "Direct-to-Video holographic read-out in quantum wells for 3-D imaging through turbid media." *Opt. lett.*, vol. 23, pp. 103-105, 1998.

R. Jones, M. Tziraki, P. M. W. French, K. M. Kwolek, D. D. Nolte, and M. R. Melloch, "Direct-to-video holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B, vol.* 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-365, 1999.

I. Lahiri, D. D. Nolte, M. R. Melloch, and M. B. Klein, "Oscillatory mode coupling and electrically strobed gratings in photorefractive quantum-well diodes," *Optics lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2 pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

D. M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct Eval.*, vol. 17, pp. 627-634, 1998.

D. D. Nolte, *Mesoscopic Pointlike Defects in Semiconductors: Deep-level Energies*, Phys. Rev. B 58, 7994-8001 (1998).

M. Dinu, I. Miotkowski and D. D. Nolte, *Magnetic Quenching of Time-Reversed Light in Photorefractive Diluted Magnetic Semiconductors*, Phys. Rev. B 58, 10435 (1998).

S. Balasubramanian, S. W. Mansour, M. R. Melloch and D. D. Nolte, *Vacancy diffusion Kinetics in arsenic-rich nonstoichiometric AlAs/GaAs heterostructures*, Phys. Rev. B 63, 033305-1 033305-3 (2000).

David D. Nolte, Manoj M. Varma, Leilei Peng, Halina D. Inerowicz, Fred E. Regnier, *Spinning-disk laser interferometers for immunoassays and proteomics: the BioCD* in Proc. SPIE vol. 5328, Microarrays and Combinatorial Techniques: Design, Fabrication, and Analysis II; Dan V. Nicolau, Ramesh Raghavachari; Eds., pp. 41-48 (2004).

Manoj M. Varma, Halina D. Inerowicz, Fred E. Regnier, David D. Nolte, *Real-time spinning: disk interferometric immunoassays*, in Proc. SPIE vol. 5328, Microarrays and Combinatorial Techniques: Design, Fabrication, and Analysis II; Dan V. Nicolau, Ramesh Raghavachari; Eds., pp 62-68 (2004).

T. Jensen, L. Kelly, A. Lazarides, and G. C. Schatz "Electrodynamics of noble metal nanoparticles and nanoparticle clusters," *Journal of Cluster Science*, vol. 10, pp. 295-317, 1999.

H. Kuwata, H. Tamaru, K. Esumi, and K. Miyano, "Resonant light scattering from metal nanoparticles: Practical analysis beyond Rayleigh approximation," *Applied Physics Letters*, vol. 83, pp. 4625-4627, 2003.

M. J. Jory, P. S. Cann, J. R. Sambles, and E. A. Perkins, "Surface-plasmon-enchanced light scattering from microscopic spheres," *Applied Physics Letters*, vol. 83, pp. 3006-3008, 2003.

K. L. Kelly, E. Coronado, L. L. Zhao, and G. C. Schatz, "The optical properties of metal nanoparticles: The influence of size, shape, and dielectric environment," *Journal of Physical Chemistry B*, vol. 107, pp. 668-677, 2003.

P. Chakraborty, "Metal nanoclusters in glasses as non-linear photonic materials," *Journal of Materials Science*, vol. 33, pp. 2235-2249, 1998.

S. J. Oldenburg, S. L. Westcott, R. D. Averitt, and N. J. Halas, "Surface enhanced Raman scattering in the near infrared using metal nanoshell substrates," *Journal of Chemical Physics*, vol. 111, pp. 4729-4735, 1999.

P. Mulvaney, "Surface plasmon spectroscopy of nanosized metal particles," *Langmuir*, vol. 12, pp. 788-800, 1996.

H. F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779-6782, 1998.

M. Minunni and M. Mascini, "Detectiion of Pesticide in Drinking-Water Using Real-Time Biospecific Interaction Analysis (Bia)," *Analytical Letters*, vol. 26, pp. 1441-1460, 1993.

C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," Analytical Chimica Acta, vol. 338, pp. 109-117, 1997.

A. Rasooly, "Surface plasmon resonance analysis of staphylococcal enterotoxin B in food," *Journal of Food Protection*, vol. 64, pp. 37-43, 2001.

G. Sakai, K. Ogata, T. Uda, N. Miura, and N. Yamazoe, "A surface plasmon resonance-based immunosensor for highly sensitive detection of morphine," Sensors and Actuators B-Chemical, vol. 49, pp. 5-12, 1998.

G. Sakai, S. Nakata, T. Uda, N. Miura, and N. Yamazoe, "Highly selective and sensitive SPR immunosensor for detection of methamphetamine," Electrochimica Acta, vol. 44, pp. 3849-3854, 1999.

E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.

A. Otto, "Excitation of Nonradiative Surface Plasma Waves in Silver by Method of Frustrated Total Reflection," *Zeitschrift Fur Physik*, vol. 216, pp. 398-410, 1968.

J. Homola, S. S. Yee, and G. Gauglitz, "Surface plasmon resonance sensors: review," Sensors and Actuators B-Chemical, vol. 54, pp. 3-15, 1999.

M. Malmqvist, "BIACORE: an affinity Biosensor system for characterization of biomolecular interactions," *Biochemical Society Transactions*, vol. 27, 1999.

M. Fivash, E. M. Towler, and R. J. Fisher, "BIAcore for macromolecular interaction," Current Opinion in Biotechnology, vol. 9, pp. 97-101, 1998.

L. D. Roden and D. G. Myszka, "Global analysis of macromolecular interaction measured on BIAcore," Biochemical and Biophysical Research Communications, vol. 225, pp. 1073-1077, 1996.

C. F. R. Mateus, M. C. Y. Huang, B. T. Cunningham, and C. J. Chang-Hasnain, "Compact label-free biosensor using VCSEL-based measurement system," Ieee Photonics Technology Letters, vol. 16, pp. 1712-1714, 2004.

P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.

G. Walter, K. Bussow, A. Lueking, and J. Glokler, "High-throughput protein arrays: prospects for molecular diagnostics," Trends in Molecular Medicine, vol. 8, pp. 250-253, 2002.

J. B. Pendry, L. Martin-Moreno, and F. J. Garcia-Vidal, "Mimicking surface plasmons with structured surfaces," Science, vol. 305, pp. 847-848, 2004.

A. G. Brolo, R. Gordon, B. Leathem, and K. L. Kavanagh. "Surface plasmon sensor based on the enhanced light transmission through arrays of nanoholes in gold films," Langmuir, vol. 20, pp. 4813-4815, 2004.

J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.

J. Coy, F. Stedt, I. Lahiri, M. Melloch, and D. Nolte, "Exciton electroabsorption moments and sum rules," Opt. Commun., vol. 176, pp. 17-29, 2000.

R. S. Rana, E. Oh, K. Chua, A. K. Ramdas, and D. D. Nolte, "Magneto-photorefractive effects in a diluted magnetic semiconductor," Phys. Rev. B, vol. 49, pp. 7941-7951, 1994.

D. D. Nolte, I. Lahiri, J. McKenna, F. R. Steldt, J. C. P. Chang, M. R. Melloch, and J. M. Woodall, "Wannier excitons in a Coulomb Cage," presented at 23rd Int. Conf. Phys. Semicond., Vancouver, Canada, 1994.

D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.

D. M. Pepper, G. J. Dunning, D. D. Nolte, J. Coy, M. B. Klein, G. D. Bacher, and B. Pouet, "Enhanced Responsivity of Photo-Induced-emf Laser Ultrasound Sensors Using Asymmetric Interdigitated Contacts," in Review of Progress in Quantitive Nondestructive Evaluation, vol. 19, D. O. Thompson and D. E. Chimenti, Eds. New York: American Institute of Physics Press, 2000, pp. 2013-2020.

Technology paper entitled "Grating-Coupled Surface Plasmon Resonance (GCSPR)"—printed from HTS Biosystems Technologies website (www.htsbiosystems.com/technology/gespr.htm) on May 2, 2005.

B. Cunningham, P. Li, and J. Pepper, "Colorimetric resonant reflection as a direct biochemical assay technique, "Sensors and Actuators B, vol. 81, pp. 316-328, 2002.

Polizzi, M. A., Plocinik, R. M., and Simpson, G. J., "Ellipsometric Approach for the Real-Time Detection of Label-Free Protein Adsorption by Second Harmonic Generation," J. Am. Chem. Soc., 126, 15, 5001-5007, 2004.

Plocinik, R. M.; Simpson, G. J., Polarization characterization in surface second harmonic generation by nonlinear optical null ellipsometry, Analytica Chimica Acta 2003, 496, (1-2), 133-142.

Musundi et al., "Approaching Real-Time Molecular Diagnostics: Single-Pair Fluorescence Resonance Energy Transfer (spFRET) Detectiion for the Analysis of Low Abundant Point Mutations in K-ras Oncogenes," J Am Chem Soc., Jun 11, 2003;125(23):6937-6945.

Konstantinos Blekas, Nikolas P. Galatsanos, Aristidis Likas, Isaac E. Lagaris: Mixture model analysis of DNA microarray images, IEEE Trans. Med. Imaging 24(7): 901-909 (2005).

Peter Bajcsy: Gridline: automatic grid alignment DNA microarray scans, IEEE Transactions on Image Processing 13(1): 15-25 (2004).

T. W. Ebbesen, H. J. Lezec, H. F. Ghaemi, T. Thio, and P. A. Wolff, "Extraordinary optical transmission through sub-wavelength hole arrays," Nature, vol. 391, pp. 667-669, 1998.

D. A. Genov, A. K. Sarychev, V. M. Shalaev, and A. Wei, "Resonant field enhancements from metal nanoparticle arrays," Nano Letters, vol. 4, pp. 153-158, 2004.

V. Koubova, E. Brynda, I., Karasova, J. Skvor, J. Homola, J. Dostalek, P. Tobiska, and J. Rosicky, "Detection of foodborne pathogens using surface plasmon resonance biosensors," Sensors and Actuators B-Chemical, vol. 74, pp. 100-105, 2001.

Michele Ceccarelli, Giuliano Antoniol: A Deformable Grid-Matching Approach for Microarray Images, IEEE Transactions on Image Processing 15(10): 3178-3188 (2006).

Luis Rueda, Vidya Vidyadharan: A Hill-Climbing Approach for Automatic Gridding of cDNA Microarray Images, IEEE/ACM Trans. Comput. Biology Bioinform, 3(1): 72-83 (2006).

Jinn Ho, Wen-Liang Hwang, Henry Horn-Shing Lu, and D. T. Lee, 'Gridding Spot Centers of Smoothly Distorted Microarray Images', IEEE Trans. on Image Processing, vol. 15, No. 2, Feb. 2006.

H. Vikalo, B. Hassibi, and A. Hassibi, "A statistical model for microarrays, optimal estimation algorithms, and limits of performance, " IEEE Transactions on Signal Processing, Special Issue on Genomics Signal Processing, vol. 54, No. 6, Jun. 2006, pp. 2444-2455.

* cited by examiner

MOLECULAR INTERFEROMETRIC IMAGING PROCESS AND APPARATUS

CROSS-REFERENCE TO RELATED APPLICATIONS

This application claims the benefit of U.S. Provisional Application Ser. No. 60/867,961, filed on Nov. 30, 2006, entitled "Molecular Interferometric Imaging Process and Apparatus," which is incorporated herein by reference.

BACKGROUND AND SUMMARY

The present invention generally relates to obtaining direct images of biological molecules distributed on surfaces designed to convert molecular phase to reflected intensity. The reflected intensity is linearly proportional to protein density. Normally invisible biological molecules are made visible by the condition of in-line interferometric quadrature established by the substrate that transduces phase to intensity. The basic principle of operation is shearing in-line common-path interferometry in which a digital interferometric image of patterns of biological molecules is acquired and referenced to a reference surface by two image acquisitions. The technique has the advantage of high speed, high sensitivity and high-resolution optical detection of biological molecules.

The Quadraspec biological compact disc system described in U.S. Pat. No. 6,685,885 requires all serial data to be acquired on a single channel. However, it may also be advantageous in signal-to-noise (and hence sensitivity) applications to acquire many channels at the same time. With the present technique, a pixel array captures a plurality of pixel readings for each image. Moreover, while conventional laser scanning techniques are time-consuming when obtaining high-resolution scans of protein spots, as well as incompatible with disc wobble when scanning spots under high magnification, the present system minimizes these problems by acquiring numerous pixels in a single exposure. In addition, the focus of the microscope can be adjusted for each well, and even at a lower magnification, an entire "well" of spots can be seen in the field of view. As such, all the protein spots are acquired at the same time and under the same conditions.

Conventional laser scanning interferometric approaches are also incompatible with real-time kinetic captures from wet samples, particularly as flow-cell plumbing is impossible, except for the use of centrifugal force to move fluids. The present system can image through a flow-cell and system, thereby making it much more like surface plasmon resonance ("SPR") systems.

However, there are several advantages of the present system over SPR techniques, particularly as the present technology is easier to implement and has a higher sensitivity than SPR technology. The present system uses a non-resonant quadrature condition, thus the operating condition is relatively insensitive to spacer thickness or wavelength. SPR systems, on the other hand, are sensitive to thicknesses and require tightly constrained wavelengths and angles. The goal of quadrature detection is to suppress noise rather than to boost signal which frees it from operating-point drift and allows it to be multiplexed over large areas. The present system also has minimal restrictions on operating wavelength or angle. The quadrature conditions can be achieved at either surface-normal or higher angles. Operation at 30° is achievable without loss in sensitivity. The optimal wavelength is also defined within a relatively broad range of tens of nanometers.

Because the operation of the present system is so robust, the noise is very low, thereby giving higher signal-to-noise ratios than SPR approaches. It is anticipated that molecular interferometric imaging will have a surface mass sensitivity of one to two orders of magnitude better than SPR. In addition, the thickness of the spacer that establishes the quadrature condition does not have to be tightly constrained. A 20% drift in thickness across a platform causes almost no change in operating sensitivity. Moreover, the loose requirements on spacer thickness and operating wavelength allows a large area to be manufactured that does not have significant sensitivity drift across the platform. This allows large-area multiplexing.

Additional features and advantages of the invention will become apparent to those skilled in the art upon consideration of the following detailed description of illustrated embodiments.

BRIEF DESCRIPTION OF THE DRAWINGS

Aspects of the present invention are more particularly described below with reference to the following figures, which illustrate exemplary embodiments of the present invention.

DETAILED DESCRIPTION OF EXEMPLARY EMBODIMENTS

Figure 1:
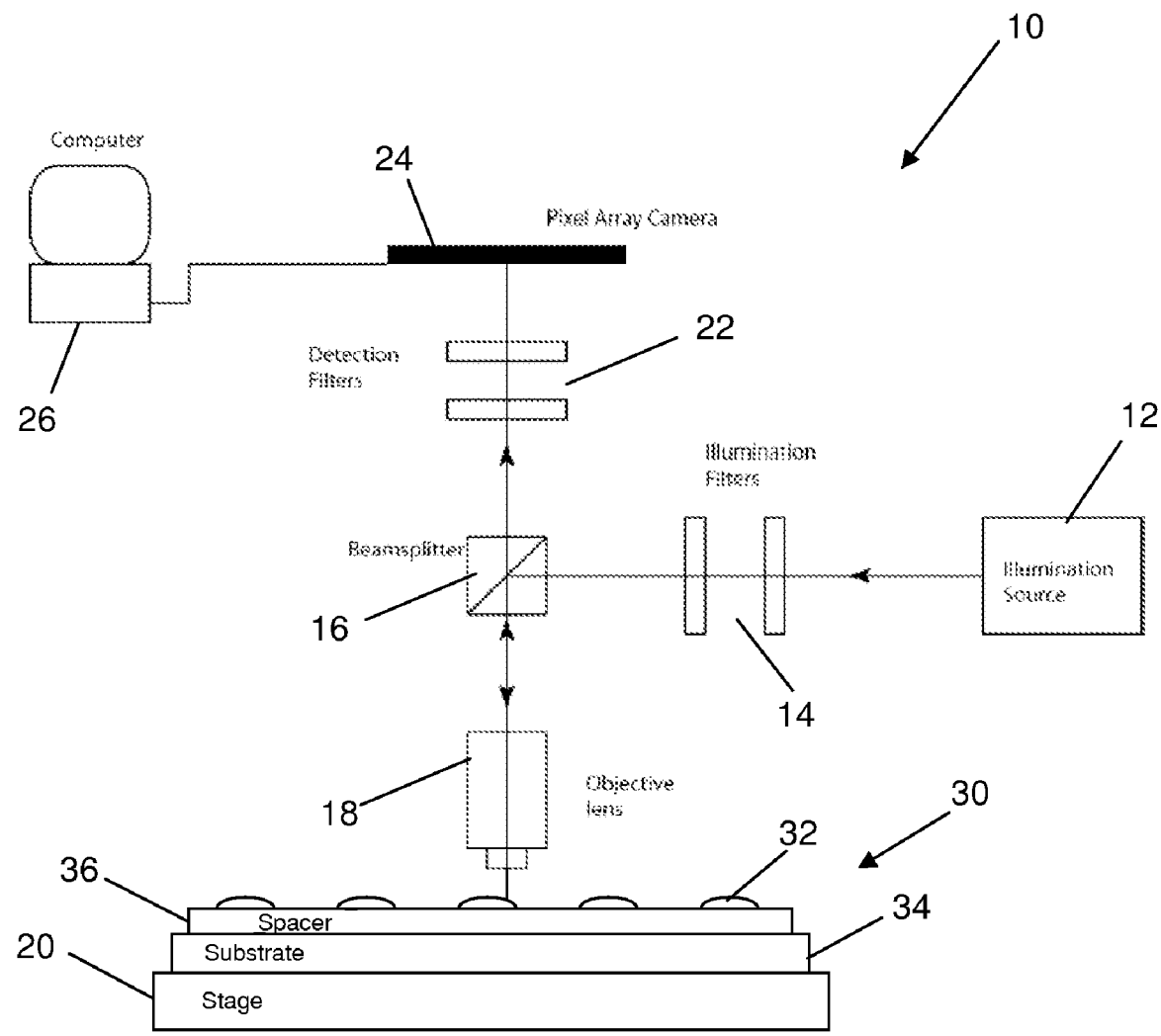
FIG. 1 is a simplified schematic drawing of an embodiment of a molecular interferometric imaging system viewing a sample.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

This application is related to U.S. patent application Ser. No. 10/726,772, entitled "Adaptive Interferometric Multi-Analyte High-Speed Biosensor," filed Dec. 3, 2003 (published on Aug. 26, 2004 as U.S. Pat. Pub. No. 2004/0166593), which is a continuation-in-part of U.S. Pat. No. 6,685,885, filed Dec. 17, 2001 and issued Feb. 3, 2004, the disclosures of which are all incorporated herein by this reference. This application is also related to U.S. patent application Ser. No. 11/345,462 entitled "Method and Apparatus for Phase Contrast Quadrature Interferometric Detection of an Immunoassay," filed Feb. 1, 2006; and also U.S. patent application Ser. No. 11/345,477 entitled "Multiplexed Biological Analyzer Planar Array Apparatus and Methods," filed Feb. 1, 2006; and also U.S. patent application Ser. No. 11/345,564, entitled "Laser Scanning Interferometric Surface Metrology," filed Feb. 1, 2006; and also U.S. patent application Ser. No. 11/345,566, entitled "Differentially Encoded Biological Analyzer Planar Array Apparatus and Methods," filed Feb. 1, 2006, the disclosures of which are all incorporated herein by this reference.

Prior to describing various embodiments of the invention the intended meaning of quadrature in the interferometric detection system(s) of the present invention is further explained. In some specific applications quadrature might be narrowly construed as what occurs in an interferometric system when a common optical "mode" is split into at least 2 "scattered" modes that differ in phase by about $N*\pi/2$ (N being an odd integer). However, as used in the present invention (and the previously referred to issued patents and/or pending applications of Nolte et al.) an interferometric system is in quadrature when at least one mode "interacts" with a target molecule and at least one of the other modes does not, where these modes differ in phase by about $N*\pi/2$ (N being an odd integer). This definition of quadrature is also applicable to interferometric systems in which the "other mode(s)," referring to other reference waves or beams, interact with a different molecule. The interferometric system may be considered to be substantially in the quadrature condition if the phase difference is $\pi/2$ (or $N*\pi/2$, wherein N is an odd integer) plus or minus approximately twenty or thirty percent. The phrase "in-phase" is intended to describe in-phase constructive interference, and "out of phase" is intended to describe substantially 180-degree-out-of-phase destructive interference. This is to distinguish these conditions, for both of which the field amplitudes add directly, from the condition of being "in phase quadrature" that describes a relative phase of an odd number of $\pi/2$.

Figure 2:
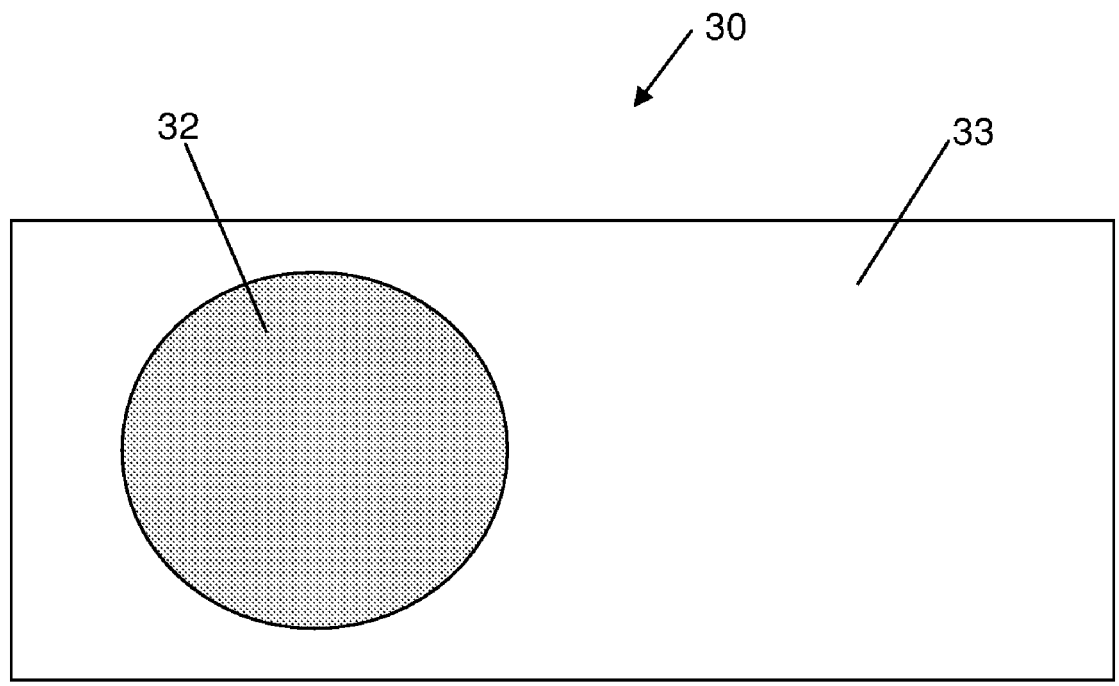
FIG. 2 is a top-view of a portion of a sample to be characterized by the interferometric imaging system.

FIG. 1 shows a basic schematic of an embodiment 10 of a molecular interferometric imaging system viewing a sample 30. The sample 30 is placed on a stage 20 of the system 10. The sample 30 is not shown to scale in FIG. 1 to ease viewing and description. The sample 30 includes a biolayer 32 that is located on a substrate 34. In some embodiments a spacer 36 is located between the biolayer 32 and the substrate 36. FIG. 2 shows a top-view of a portion of the sample 30 to be characterized by the system 10. The sample 30 includes the biolayer 32 that is to be analyzed by the system 10 and a land 33 that acts as a reference surface. When there is a spacer 36, the spacer 36 can act as the land 33; and when the biolayer 32 is applied directly to the substrate 34, the substrate 34 can act as the land 33. As an example, one embodiment of the sample 30 can include silicon as the substrate 34 with an oxide layer as the spacer 36, and the oxide thickness selected to put the system in an in-line quadrature condition (typically 120 nm). In this embodiment, the biolayer 32 can include a plurality of spots containing a capture antibody deposited on the spacer 36, and when a specimen containing the analyte is applied to the sample 30, the analyte is captured by the antibody in the biolayer 32.

A radiation beam from an illumination source 12 passes through illumination filters 14 and into a beam splitter 16 which directs the incident beam through an objective lens 18 on onto the sample 30. The reflected beam from the sample 30 passes back through the objective lens 18 and the beam splitter 16. The reflected beam then passes through detection filters 22 and onto a pixel array camera 24. The pixel array camera 24 is connected to a computer 26 which stores the reflected image of the sample 30. If the light source 12 is a laser tuned to the appropriate quadrature condition for the spacer 36 of the sample 30, then either or both of the filters 14 and 22 are optional. However, if the light source 12 is a broad-band source (such as an incandescent light or a halogen lamp) then at least the illumination filters 14 would be necessary.

A differential composite image is obtained by acquiring an image of the biolayer 32 and an image of the land 33, and then differencing the two images. The adjacent land acts as the reference surface for illumination normalization.

The substrate 34 and spacer 36 are configured to convert phase modulation to reflected intensity so that it can be detected and imaged directly by the pixel array 24. This phase-to-intensity conversion takes place through in-line quadrature interferometry which is described in U.S. patent application Ser. No. 11/675,359, entitled "In-Line Quadrature and Anti-Reflection Enhanced Phase Quadrature Interferometric Detection," which was filed on Feb. 15, 2007, and is hereby incorporated herein by reference. The light reflected from the biological molecules has a quadrature condition relative to light reflected from an in-line reference surface. This converts the phase modulation caused by the light interacting with the molecular dipoles to interfere in the far-field with the reference light to create the intensity modulation that is proportional to the phase modulation. The equation describing this process is:

$$\Delta I = 2\sqrt{I_{ref} I_{signal}} \Delta\phi \qquad (1)$$

where the phase modulation caused by the molecules is:

$$\Delta\phi = \frac{4\pi}{\lambda}(n_b - n_m)d \quad (2)$$

where d is the effective thickness of the biolayer, $n_b$ is the refractive index of the biolayer, and $n_m$ is the refractive index of the surrounding medium. From a molecular point of view there is not a biolayer but rather a scattered distribution of molecules on the surface. Then the modulated phase is:

$$\Delta\phi = \frac{4\pi}{\lambda}(n_b - n_m)\frac{2\pi r_m^3}{3r_s^2} \quad (3)$$

where $r_m$ is the molecular radius of gyration, and $r_s$ is the average molecular separation on the surface. The refractive index in this case is the refractive index associated with the individual molecules.

The intensity modulation $\Delta I$ caused by the biolayer 32 is often small, in the range of a few percent of the total intensity. Therefore, spatial variations in the illumination can be nearly as large as the protein signal. The land 33 can be used to normalize this background variation and make the protein structures clear. The land 33 has substantially no protein on it and acts as a normalization surface.

Figure 3:
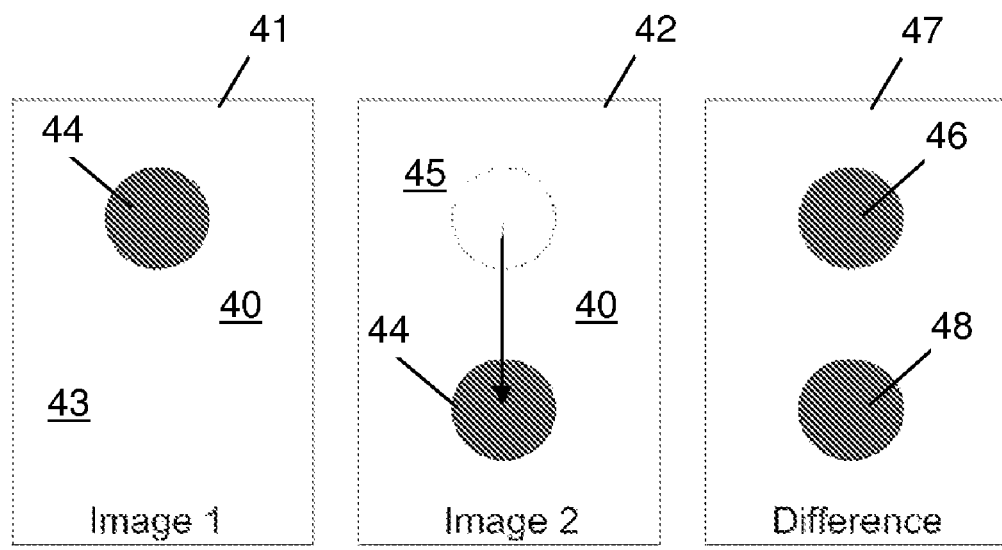
FIG. 3 illustrates a sample method for normalizing the background variation with a differential image.

FIG. 3 shows one example of normalizing the background variation with a differential image. In this example, a portion of a biological compact disc 40 is shown that has a protein spot 44, a lower adjacent land 43, and an upper adjacent land 45. A first image 41 is taken of the protein spot 44 using the imaging system 10 which includes the lower adjacent land 43. The disc 40 is shifted in the field of view of the system 10 and a second image 42 is taken of the protein spot 44 using the imaging system 10 which includes the upper adjacent land 45. The normalization procedure uses the two images 41 and 42. A composite differential image 47 is computed on a pixel-by-pixel basis as:

$$I_{Diff} = 2\frac{(I_A - I_B)}{(I_A + I_B)} \quad (4)$$

where $I_A$ is a pixel value from the second image 42 and where $I_B$ is the corresponding pixel value from the first image 41. The composite differential image 47 includes two versions of the protein spot 44: a negative difference version 46 (the land 45 of image 42 minus the protein spot 44 of image 41) and a positive difference version 48 (the protein spot 44 of image 42 minus the land 43 of image 41). The spot information in the image pair 46, 48 is the same, but the background is different. The difference compensates for the spatial variations in the illumination, and can be used to produce an image of the protein spot 44. It is preferable to use a combination of the image pair 46, 48 in subsequent data analysis to provide for an average of the protein spot 44, but either 46 or 48 can be used alone. The magnitude of the spot height in the difference images 46, 48 are proportional to the amount of protein present in the spot 44.

The land adjacent to a biological spot should be flat and clean to provide a good normalization surface. The land on both sides of a spot can be used for a single shift in one direction, but multiple shifts could also be used to try to balance directional systematics on the disc or wafer. For a single difference image of a spot and adjacent land, no registration is needed since the land is generally homogeneous. However, when taking many difference images and averaging them, then registration of the multiple difference images is preferred. Algorithms and software packages are commercially available to register images in microscopy. The normalization surface is not an interferometric reference surface. The interferometric reference surface is in-line, not lateral. The normalization surface takes effect after the reference-surface has already converted phase to intensity. The normalization removes spatial variations in the illumination.

The following description provides greater detail on the eight basic elements of the embodiment of the in-line molecular interferometric imaging system 10 shown in FIG. 1. There are many possible alternative embodiments for each of these elements.

The illumination source 12 could be any one of numerous illumination sources known in the art (e.g., incandescent; halogen; LED). The light source 12 can be coherent or incoherent, and single color or multiple color. High photon flux is provided by an LED or a superluminescent diode, but a more basic embodiment would be a white light source that is filtered.

The illumination filters 14 can be any one of numerous illumination filters known in the art (e.g., color; polarization; Fourier and image masks). Illumination filters can convert white light into single color or multiple color light. Multiple colors could be selected to coincide with the two opposite in-line quadrature conditions set by the substrate. By matching the detection filters 22 to the illumination filters 14 differential color composite images can be composed to isolate protein relative to scattered light or absorbed light. If the filters are in the UV, then protein or DNA spectroscopy becomes possible because of the optical transitions in the UV. The combination of in-phase with quadrature information in interferometry provides a complete picture of the material optical transitions (refractive index and absorption).

The illumination filters 14 can also be used to provide Fourier filtering of the beam from the illumination source 12. This could be used, for example, to present illumination that selects phase contrast on the disc or plate. If the disc or plate at a selected wavelength is in the anti-node condition (maximum field at the substrate surface), then phase contrast images can be acquired at that wavelength. If multiple wavelengths are used, then the phase contrast image can be combined with the quadrature images obtained at other wavelengths.

The illumination filters 14 can also be used to provide polarization of the light from the source 12 which can be informative if the molecules are oriented on the substrate.

The objective lens 18 could be any one of numerous objective lens systems known in the art (e.g., coverslip corrected; coverslip uncorrected; long working distance). The objective lens 18 is the imaging element in the system. It can be configured to work with or without coverslips. In the case of microfluidic systems, the objective should have a working distance that is compatible with the coverings over the microfluidic systems. In the case of conventional 96-well plate, the objective lens should have a long working distance. This can sometimes reduce the magnification, but a large numerical aperture (NA) system can retain high magnification even for long working distance.

The substrate 34 could be composed of numerous materials (e.g., quadrature conditions: 120 nm oxide on silicon, 100 nm oxide on silicon, 80 nm oxide on silicon; SiN on silicon, anti-reflective (AR) coatings on glass, dielectric stacks on glass; Substrate formats: Quadraspec biological compact disc substrates, 96, 384, 1536-well plate substrates; and microfluidics). The substrate converts phase modulation to intensity modulation by interference effects set up by the substrate structure. This can be accomplished by a wide range of structures that have multiple layers ranging from a single layer to possibly hundreds.

One embodiment uses a substrate of thermal oxide grown on silicon. Thicknesses of 120 nm and 80 nm provide opposite quadrature at a wavelength of 635 nm. A thickness of 100 nm provides for phase-contrast imaging if a Fourier filter is used in the illumination and detection Fourier planes. Shifting of quadratures is also possible by choice of wavelength. Therefore, any multilayer substrate that produces partial reflections that may differ in phase by substantially $\pi/2$ will produce the appropriate phase-to-intensity conversion that is needed. An antireflection structure tuned near quadrature, or more generally dielectric stacks, can be used.

Substrate formats can be highly varied. A Quadraspec biological compact disc system format is possible, with direct imaging of protein spots in the wells. Or conventional 96-well plates can be used with protein spots printed onto an optically flat bottom that has been coated with dielectric layers that provide the quadrature condition. The substrates also can consist of microfluidic systems that deliver sample to the protein spots in real time. The molecular interferometric imaging process works when the system is immersed in water or biological fluids. The effects of the fluid matrix are cancelled by comparing the mass increase of a specific spot to land and also to non-specific spots. Therefore, the near-surface sensitivity of SPR and BioLayer Interferometry ("BLI") are not necessary because the full-field image allows reference values to be acquired simultaneously by which the matrix effects are subtracted.

The biolayers 32 can be structured in any of numerous ways known in the art (e.g., spots; ridges; checkerboard). The biological molecules can be patterned on the disc in many possible configurations. The most common are spots, ridges and checkerboards. Periodic ridges enable Fourier image processing techniques in one-dimension, and checkerboard patterns allow Fourier image analysis in two-dimensions. Alternating ridges of specific and non-specific molecules constitute an embodiment of differential encoding.

The stage 20 can also be structed in various embodiments (e.g., rotation; translation; dither). The stage motion enables normalization. Shifts of the stage 20 can take many formats that are chosen to be optimal for the different substrate formats. A rotation stage is perhaps most compatible with compact disc systems, while X-Y translation is most compatible with 96-well plates.

Dithering, which is another option for stage motion, is a periodic shifting back and forth. This might be used during kinetic binding experiments to better track the added mass. Dithering combined with synchronized pixel array image acquisition can be considered to be a type of pixel array lock-in approach.

The detection filters 22 can be any one of numerous detection filters known in the art (e.g., color; polarization; Fourier and image masks; phase contrast). The detection filters are placed before the pixel array 24. They may reside on image planes or Fourier planes. If the detection filters 22 are in the Fourier plane, they may include phase and amplitude masks. These masks can perform important functions such as phase contrast imaging. In this case, a $\pi/2$ mask on the Fourier plane can produce a phase contrast image on the pixel array 24.

Other detection filters that may reside on or off the image or Fourier planes would be wavelength and polarization filters that are matched to the respective illumination filters. These can allow multi-wavelength operation, for instance, or single wavelength operation. It would also be possible to place dichroic beamsplitters before the image detection to separate spatially images of different colors. Multiple dichroic beamsplitters would enable multiple different color images that could all be detected individually with individual cameras. Alternatively, a rotating filter wheel could sequentially switch color filters synchronized with the camera acquisition. This would enable multiple wavelength images to be acquired using only a single camera.

The pixel array 24 can be any of numerous image detectors known in the art (e.g., CCD; complementary metal oxide semiconductor ("CMOS"); pixel arrays; red, green and blue ("RGB"); megapixel; synchronization). Many formats are possible for the image detection. In one embodiment, the image detection is through a CCD or CMOS or pixel array device. Any device that has separate spatial channels to detect light at multiple locations on the image plane would be applicable. A pixel format having a high pixel density can be used, resulting in, for example, from 1 megapixel images up to 15 megapixel or greater images. The "dead" space between pixels can be small. The pitch between pixels can also be small to reduce the requirements for high magnification.

Synchronization of the camera with an external trigger can be used to capture sequential images as some property is changed in the detection mode. For instance, synchronizing the camera with switching color filters, or synchronizing the camera with platform displacement or dither.

The camera 24 can be monochrome, using multiple color filters to acquire multicolor data—or the camera 24 can be a 3-color-channel array that detects red, green and blue individually. The oxide thickness of the substrate 34 can be changed to match the two quadrature conditions of the substrate to the red and blue channels on the camera, with the green channel representing the null condition in-between. This would allow full detection sensitivity for the red and blue, and enable full differential sensitivity for the green channel.

Advantages and improvements of the methods of the present invention are demonstrated in the following examples. The examples are illustrative only and are not intended to limit or preclude other embodiments of the invention.

Images of proteins on thermal oxide on silicon in the quadrature condition using a color filter on a conventional microscope have been acquired. These images were near the quadrature condition. First and second images were acquired with the platform displaced in-between acquisitions. The differential composite exhibited high sensitivity to protein and low sensitivity to background effects.

Figure 4:
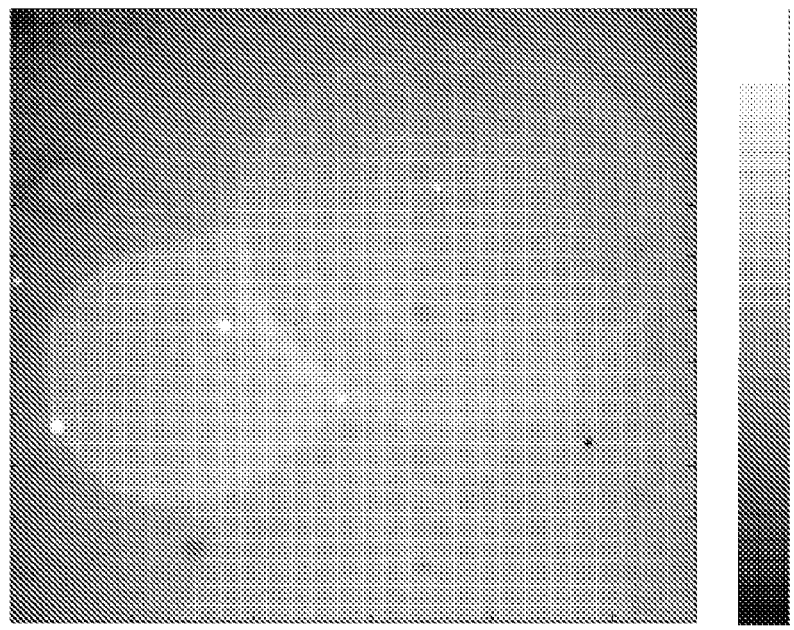
FIG. 4 is a direct image under 40× magnification of a protein spot on 120 nm oxide thickness acquired with a 12-bit CCD camera.

A direct image under 40× magnification of a protein is shown in FIG. 4 as a grayscale. The protein was IgG printed on 120 nm oxide on silicon. The spot was printed using a Scienion printer with approximately 100 picoliters of liquid volume. The substrate is an in-line quadrature Quadraspec biological compact disc with functionalized surface chemistry. The full range of the color bar is approximately 4 nanometers. The image was acquired with a 12-bit CCD camera. The intensity modulation caused by the protein is generally a few percent. The protein height is approximately a nanometer. The brighter tail on the lower left is the wash-off tail which is several nanometers high. The variability in the image is mostly caused by inhomogeneous illumination and also by dust in the optics. The background variability is smaller than, but still comparable to, the magnitude of the protein signal.

Figure 5:
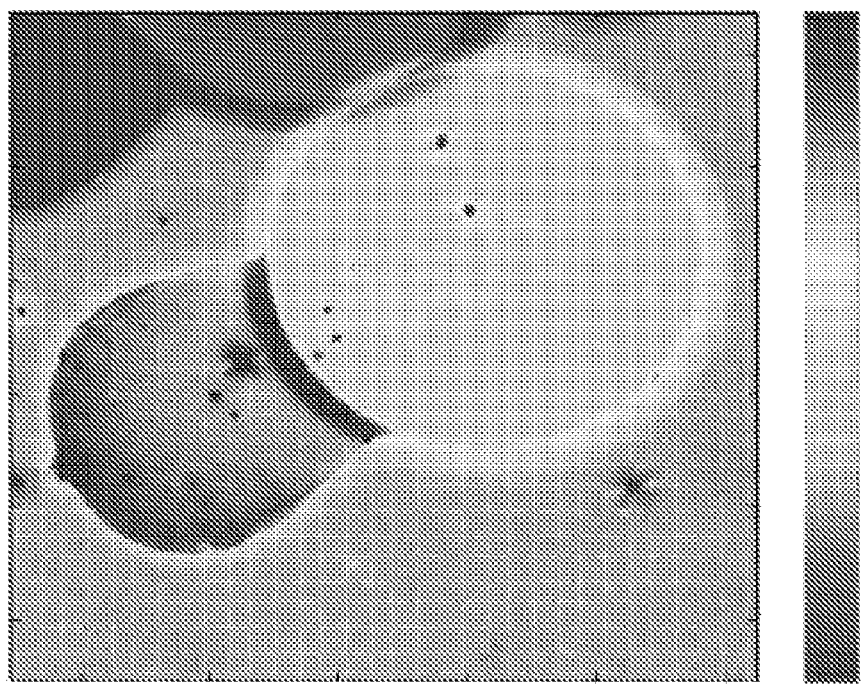
FIG. 5 is a differential composite image of the protein spot shown in FIG. 4 after shift and acquisition in which the color is proportional to the protein height.

The protein spot after execution of the platform shift and the calculation of the differential composite image is shown in FIG. 5. Most of the background variability is removed by the normalization procedure of Equation 4. The protein heights in the image are several nanometers.

Figure 6:
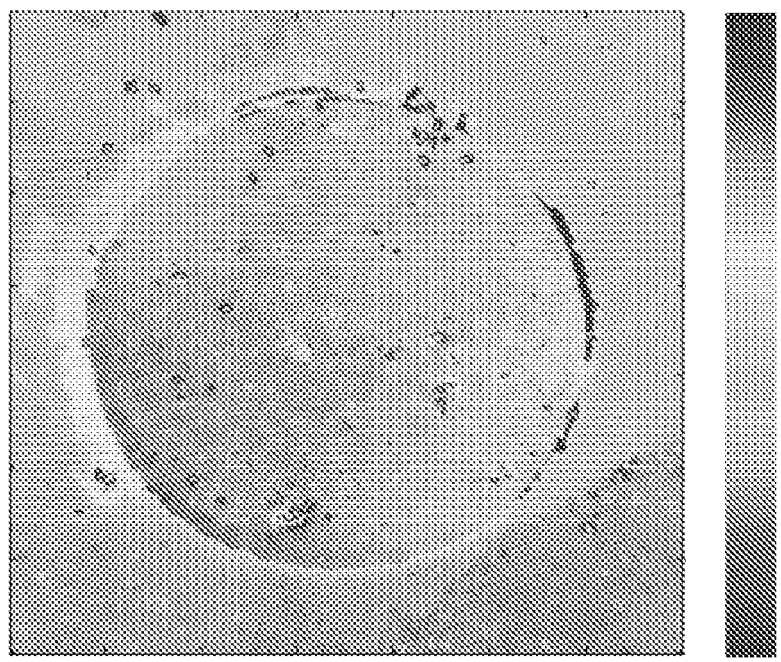
FIG. 6 is an example of a uniformly printed 120 micron diameter protein spot with a height of 1-2 nm and the full range scale of the image being −2 nm to +2 nm.

FIG. 6 shows a high resolution protein image of a uniformly printed 120 micron diameter protein spot. The protein height is approximately 1-2 nanometers. The full range scale is −2 nm to 2 nm.

Figure 7:
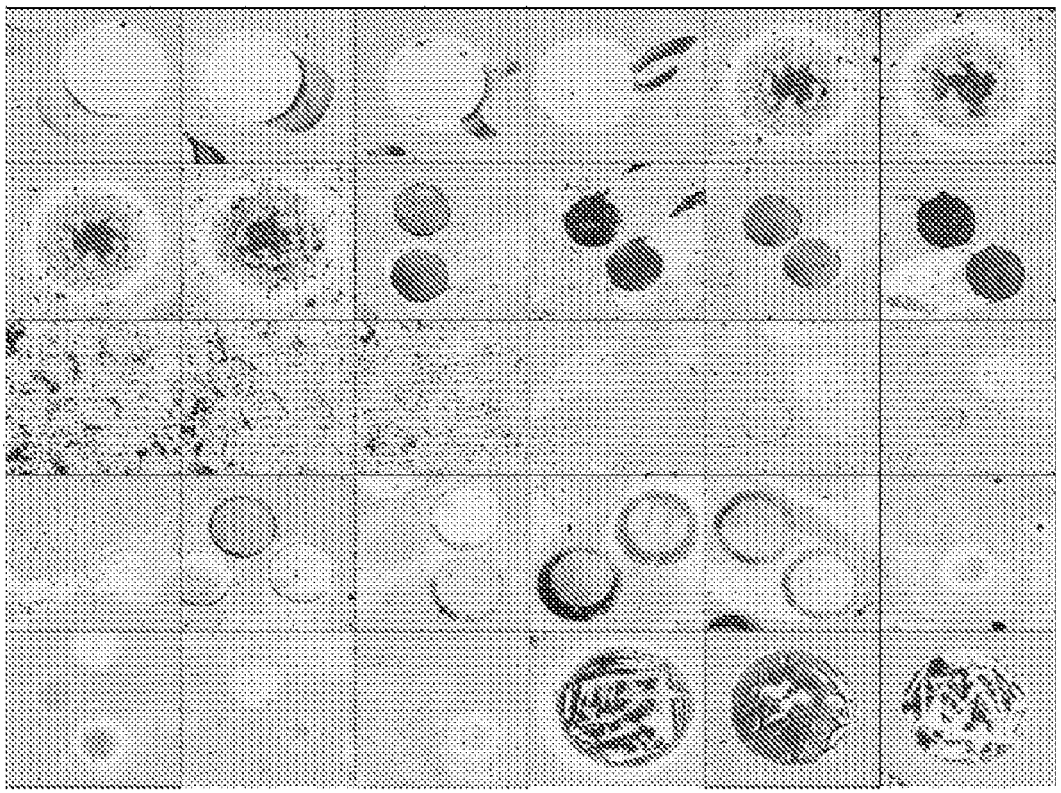
FIG. 7 is a composite of several differential composite images of many different protein spots, all approximately 100 microns in diameter, on many discs showing many different morphologies.

A photo gallery of many differential composite images for many types of spot morphologies is shown in FIG. 7. The protein spots are all approximately 100 microns in diameter. The images were acquired from many different wafers using many different chemistries. The protein spot heights in all cases are from about half a nanometer to several nanometers.

Figure 8:
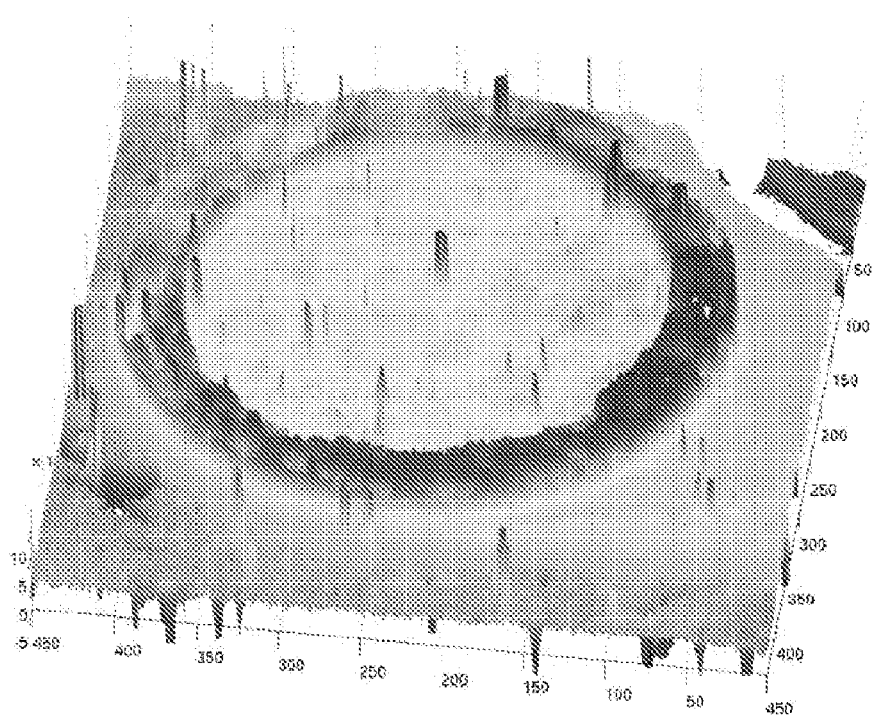
FIG. 8 shows a pseudo-three dimensional image of surface morphology of a printed spot with a pronounced outer ring having a ring height of approximately 0.7 microns.

FIG. 8 shows a pseudo three-dimensional image of surface morphology of a printed spot with a pronounced outer ring. The high circular rim is caused by preferential protein deposition as the spot evaporates. The ring height is approximately 0.7 nm.

Figure 9:
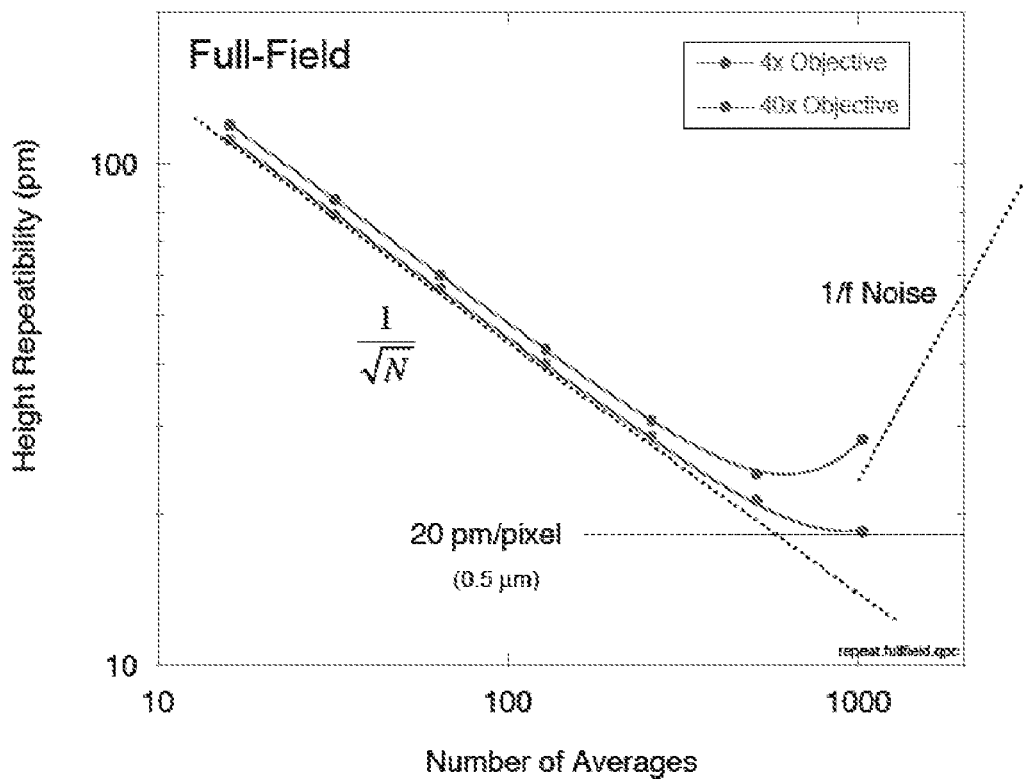
FIG. 9 shows a graph of the height repeatability (standard deviation) in picometers as a function of the number of averaged images at both 40× and 4× objective magnification.
Figure 10:
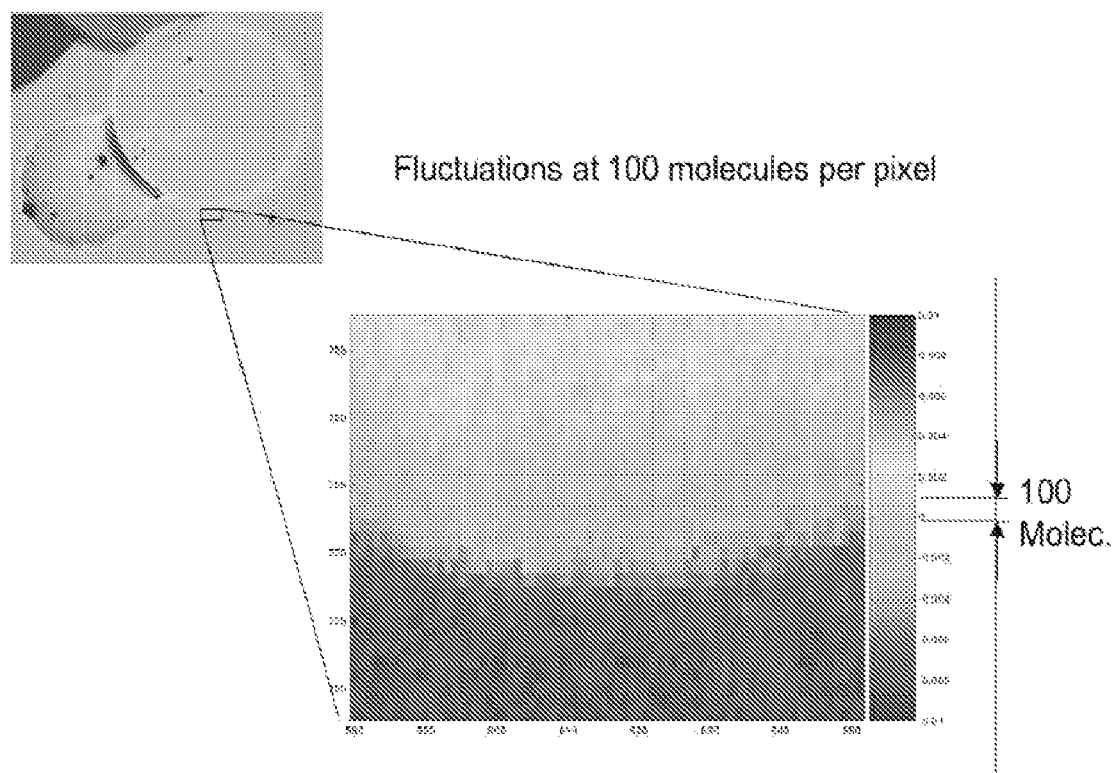
FIG. 10 shows a pixel to pixel fluctuation of approximately 100 molecules for 1024 averaged images.

Repeatability experiments were performed in which pixel variability was measured as a function of the number of frames that were acquired and averaged. The height repeatability (standard deviation) is plotted in FIG. 9 as a function of the number of acquisitions for both 40× and 4× objective magnification. The standard deviation of the differenced images decreases inversely with the square root of the number of acquisitions up to approximately 1024 images. For more images than this, long-term drift begins to dominate, representing 1/f noise. The minimum standard deviation was 20 picometers per pixel. The fluctuations for 4× are not much higher. The pixel size in the case of 40× is 0.5 microns, and for 4× is 5 microns. When the platform shift is used to normalize the pixel values, the standard deviation increases by about a factor of 3 to 60 picometers. The equivalent number of IgG molecules that this corresponds to is approximately 100 molecules. This is illustrated in FIG. 10, in which the pixel-to-pixel fluctuations are at the level of approximately 100 molecules on the edge of the printed protein spot.

Figure 11:
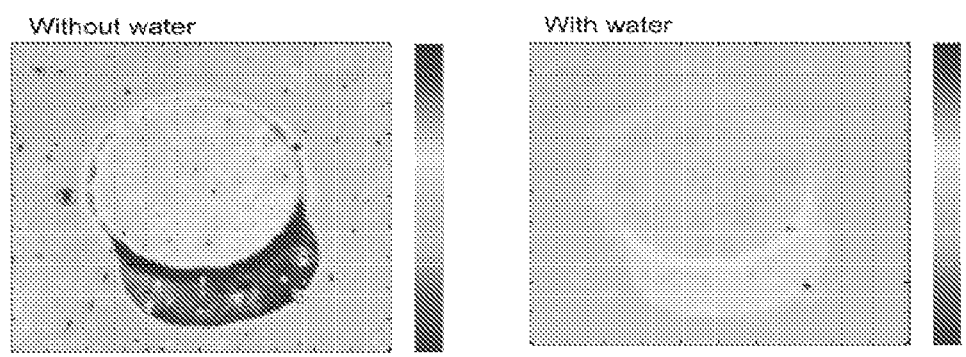
FIG. 11 shows a differential composite image of a protein without water and under water, showing that the protein spot remains visible under water with approximately a factor of three reduction in signal intensity.

Embodiments of the present invention can also operate under water. The protein differential composite image is shown in FIG. 11 under the two conditions of dry and wet. The protein was under a glass coverslip. Water was introduced between the slip and the disc surface. The protein is still visible, with approximately a factor of 3 reduction in the signal intensity. At the same time, dust and other background noise also decreased by about a factor of 3 keeping the signal-to-noise ratio approximately constant. Detection sensitivity is set by the signal-to-noise ratio. Therefore, operation of the molecular interferometric imaging under water is feasible. This enables kinetic capture experiments in which binding could be tracked in real time. To detect real time binding, either the platform is dithered with synchronized image acquisition, or else successive images would be differenced and normalized to detect the binding.

These data also demonstrate the ability to use the known refractive index of water to measure the refractive index of the protein. The protein signal under water is still a positive signal. This requires that the refractive index of the protein be larger than the refractive index of water. The refractive index of the protein is calculated by solving the equation:

$$\frac{n-1}{n-1.33} = \frac{\Delta l_{dry}}{\Delta l_{wet}} \quad (6)$$

The refractive index measured for the protein layer in this way is approximately n=1.5.

Figure 12:
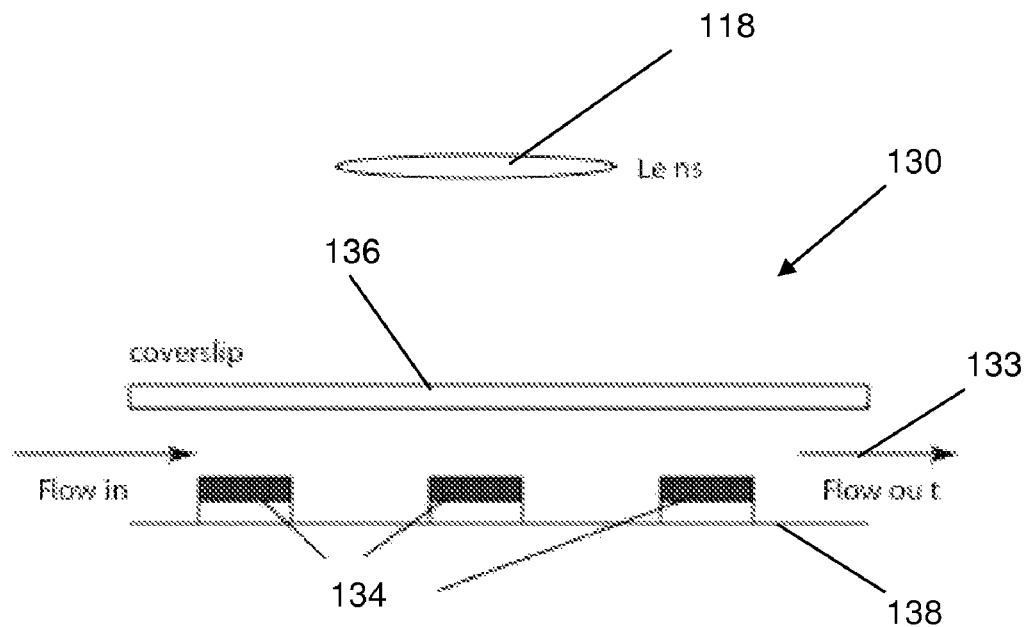
FIG. 12 shows a simplified diagram of an arrangement for directly imaging a sample through a liquid using molecular interferometric imaging.

The capability to directly image through water using molecular interferometric imaging enables real-time binding experiments. A simplified diagram of the experimental arrangement is shown in FIG. 12. The optical arrangement is similar to that of FIG. 1, and for clarity only the objective lens 118 is shown. However, now a sample 130 is to be characterized that has an active flow of liquid in the direction of arrow 133 over antibody spots 134 on a support layer 138. The lower white part of the spots 134 represents the antibody and the upper dark part of the spots 134 represents the captured analyte. The support layer 138 can be the top surface of a substrate or oxide layer.

The imaging is performed through a top glass coverslip 136 and through the liquid. The liquid is a potential source of background signal because it contains the analytes that are being captured out of solution by the antibody spots 134. However, the captured mass is enhanced relative to the background analyte by the anti-node condition that is at the surface of the support layer 138. The field strength is twice as high at the protein spot 134 compared to the average over the liquid volume. Furthermore, in molecular interferometric imaging, continual image-pair acquisition is taking place that compares the mass over the spot 134 to the mass captured by adjacent land 138. The overlying fluid remains the same in both images and hence is subtracted. Another approach to ameliorate the background in the liquid could be to periodically flush the system with buffer, during which image pairs are acquired. In this case, the overlying liquid is free of the analyte. A combination of both approaches might give the best balance in terms of sensitivity to bound analyte.

Figure 13:
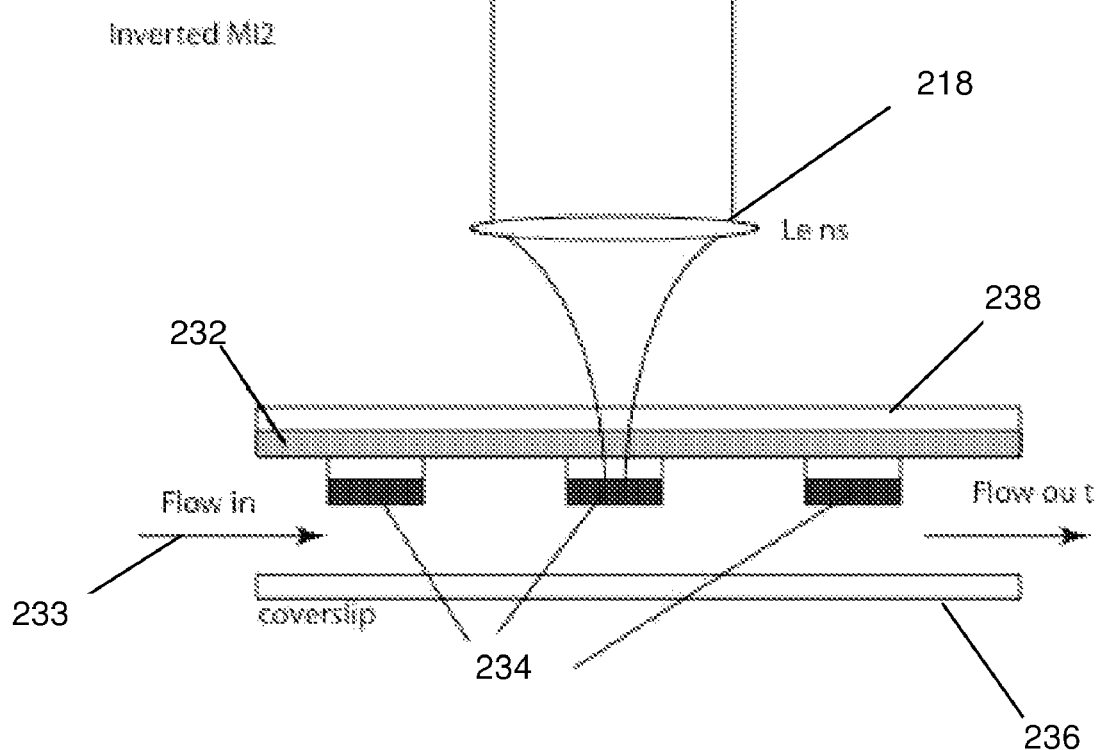
FIG. 13 shows a simplified diagram of an arrangement for directly imaging a sample that is immersed in liquid using molecular interferometric imaging without imaging through the liquid.

The in-line approach also makes it possible to interrogate the proteins without going through the liquid. One embodiment of this is shown in FIG. 13. The imaging geometry is the same as that of FIG. 12, but now the light passes through the upper glass slide 238 that carries the antibody spots and the bound analyte 234. The in-line quadrature condition is established by appropriate dielectric layers 232. A top reflection can be the reference wave, and the reflection off the protein-carrying surface can be the signal wave. The addition of mass on the protein spot 234 alters the phase of the reflected light that is detected through the in-line quadrature interfeormetry at the camera. This approach has the advantage that the light does not pass through the liquid layer containing the analyte.

Figure 14:
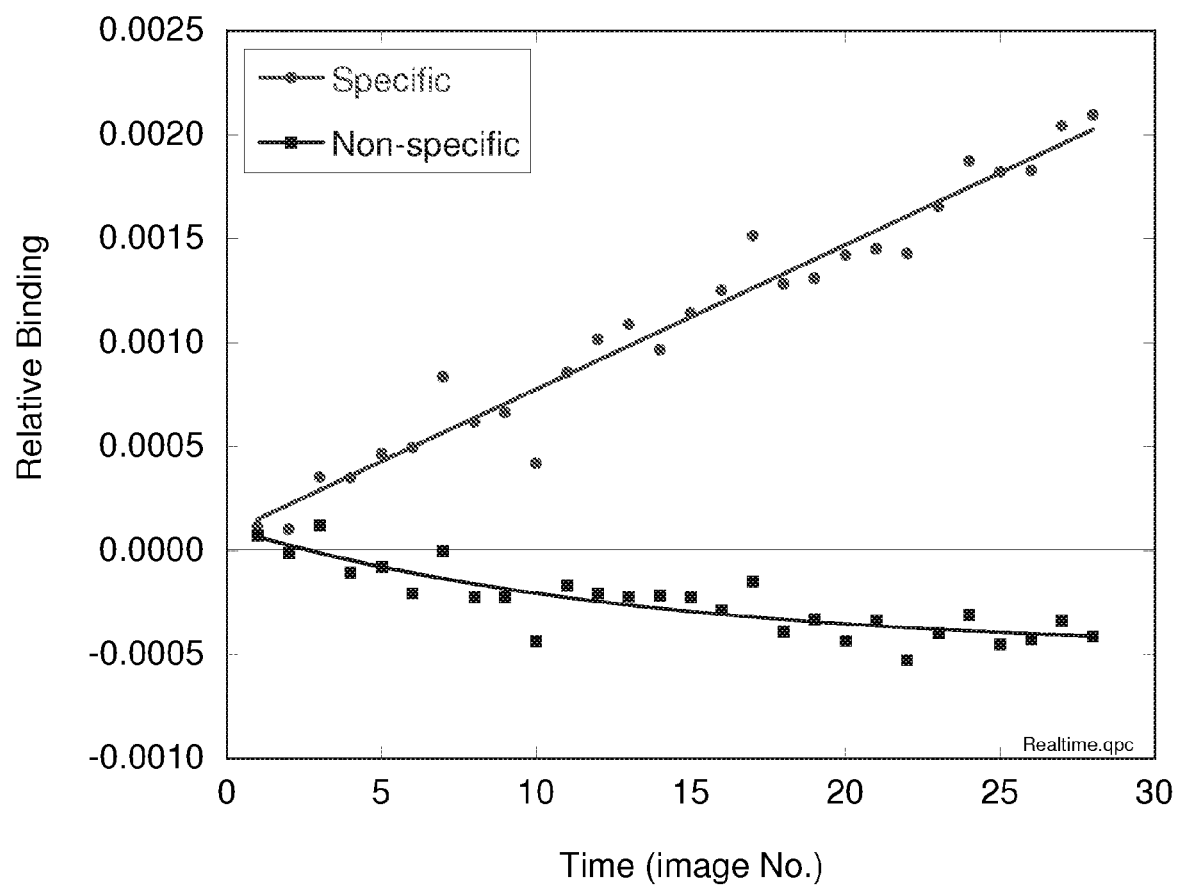
FIG. 14 shows a graph of experimental data from real-time binding showing an increase in spot height for the specific spots, and a decrease in spot height for the non-specific reference spots versus image frames collected at 40 second intervals.

FIG. 14 is a graph of experimental data from real-time binding showing an increase in the spot height for the specific spots, and a decrease in the spot height for the non-specific reference spots. The decrease in spot height for the non-specific reference spots is due to wash-off. The time between frames is 40 seconds. The analyte concentration was 40 ug/ml. During the collection of 28 images (1,080 seconds or 18 minutes) the relative binding on the specific spots increased from approximately 0.0001 to 0.0020 while the relative binding on the non-specific spots decreased from approximately 0.0001 to −0.0004.

Figure 15:
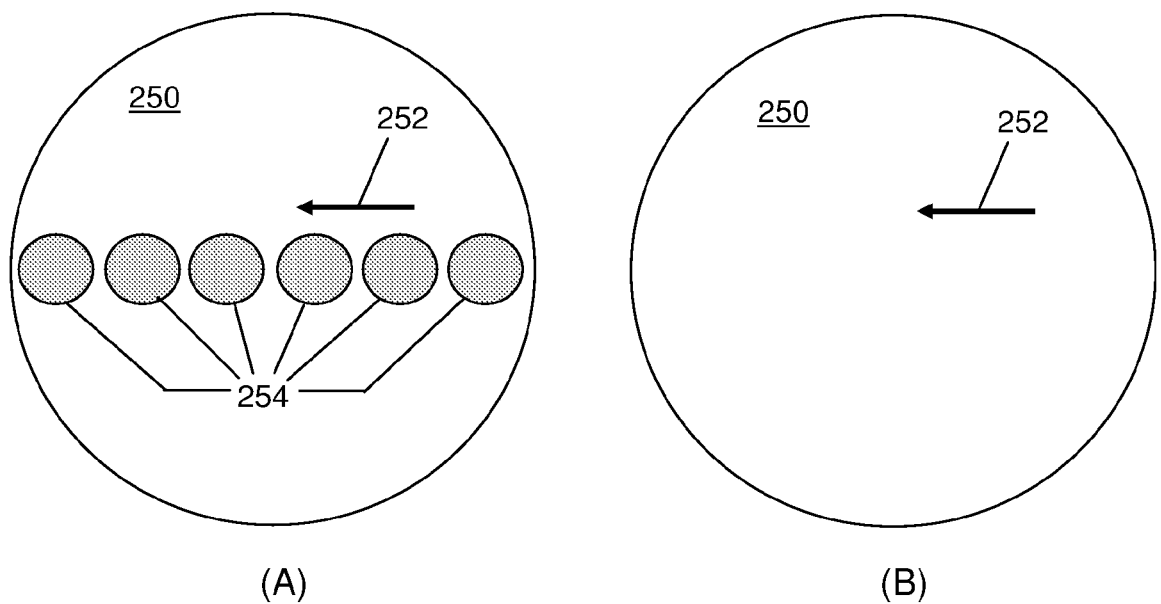
FIG. 15A illustrates a multiple exposure image of a protein spot as it travels across the field of view.
FIG. 15B illustrates a multiple exposure image of a uniform land as it travels across the field of view.

The sensitivity of the molecular interferometric imaging approach can be enhanced by increasing the data acquisition rate, especially with respect to disc translation from spot to spot. A simple embodiment is to utilize a slowly spinning disc or translating plate as shown in FIG. 15. The pixel array of the system has a field of view 250 and the sample has a protein spot 254. In part (A) of FIG. 15, the camera shutter is opened and closed on a time scale that is short relative to the motion of the protein spot 254. This results in a multiple exposure of the same protein spot 254 as it travels across the field of view 250. In the case shown in FIG. 15(A), an image with six multiple exposures of the protein spot are captured at different positions in the field of view 250. For normalization purposes, the same operation can be done for the adjacent land as shown in part (B) of FIG. 15. In the case shown in FIG. 15(B), an image with six multiple exposures of the land, which is substantially clean and uniform, is captured at different positions in the field of view 250. Different magnifications can be used to capture more or less protein spots in the field of view.

Each exposure is of the same protein spot 254, providing averaged detection statistics, and the multiple exposure image of the protein spot is referenced to a multiple exposure image of different parts of the land, providing averaging over the land topology which can be a limiting factor in single-pair molecular interferometric imaging. This approach would not necessarily need a larger memory, because the shutter could open and shut many times prior to reading out the digital image. The data in this case is a repeated exposure. Many images of the spot and land are acquired in only one multiple exposure image.

Figure 16:
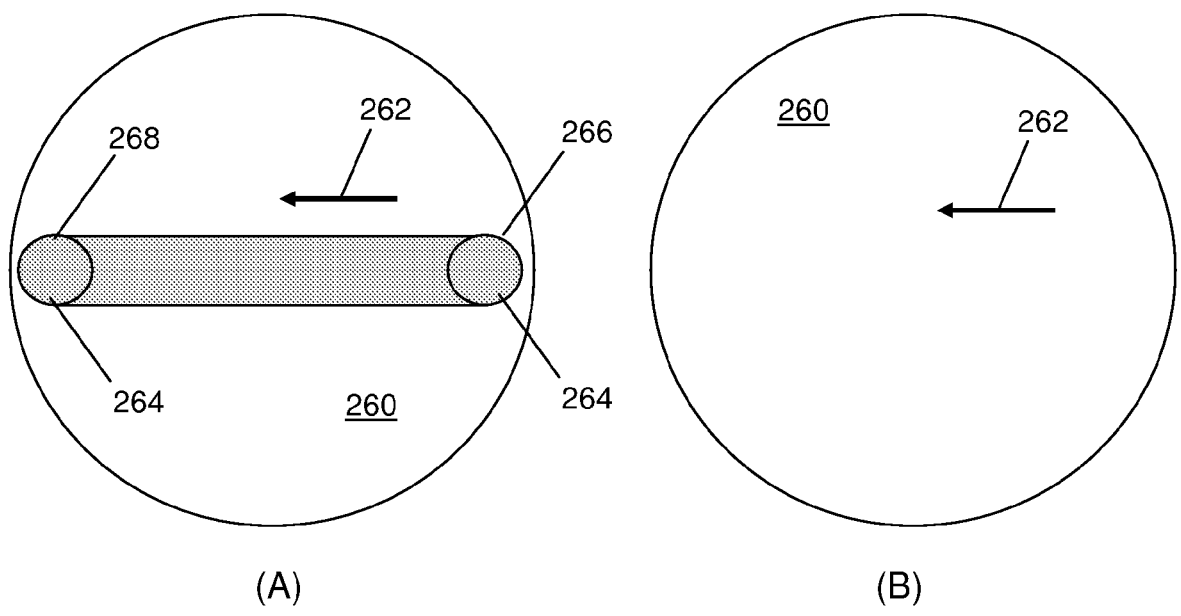
FIG. 16A illustrates a time-lapse image of a protein spot as it travels across the field of view.
FIG. 16B illustrates a time-lapse image of a uniform land as it travels across the field of view.

Another embodiment that utilizes a continuously spinning disc or translating plate, and takes the last embodiment to its limiting behavior, is time-lapse exposure while the disc is continuously spinning or plate is continuously moving as shown in FIG. 16. The pixel array of the system has a field of view 260 and the sample has a protein spot 264. In part (A) of FIG. 16, the camera shutter is opened when the spot 264 is at position 266 at the edge of the field of view 260. The shutter remains open while the protein spot 264 crosses the field of view 260 and finally closes when the spot 264 reaches position 268 at the other side of the field of view 260. For normalization purposes, the shutter remains open for the same time period as the adjacent land as shown in part (B) of FIG. 16 traverses the field of view 260 in the direction of arrow 262.

While the spot 264 is moving across the field of view 260, the pixel array records an average intensity that is a combination of the protein spot 264 and the adjacent land on the trailing side and appears as a "swath". The average intensity over the swath provides a means for averaging spatial illumination drift, which can be a limiting factor in molecular interferometric imaging.

Rapid acquisition of the reference surface improves the results of the molecular interferometric imaging system. The idea of disc translation, taken to the limiting case of having the disc spin, is one type of approach, but other approaches are also possible. The purpose of the reference surface in molecular interferometric imaging is to provide intensity normalization. This is a relatively easy requirement that is much simpler than the reference surfaces that are required for non-common-path interferometers in which the reference surface distance must be stabilized to within a small fraction of a wavelength. Therefore, all that is needed is a means of introducing the reference surface as a separate image to be acquired.

One embodiment is to have a high-speed mirror that rapidly switches back and forth between a protein spot and a physically separated reference surface. The image acquisition by the camera can be synchronized with the mirror motion.

Another embodiment is to have a mirror on a spinning disc that is between the protein layer and the objective lens. The disc would have a clear aperture to image the protein spot, then the mirror moves between the lens and the protein spot. A reference image is acquired at the moment the mirror is between the lens and the protein spot. A similar embodiment uses an oscillating galvonometer that switches the image between the reference surface and the protein spot.

Figure 17:
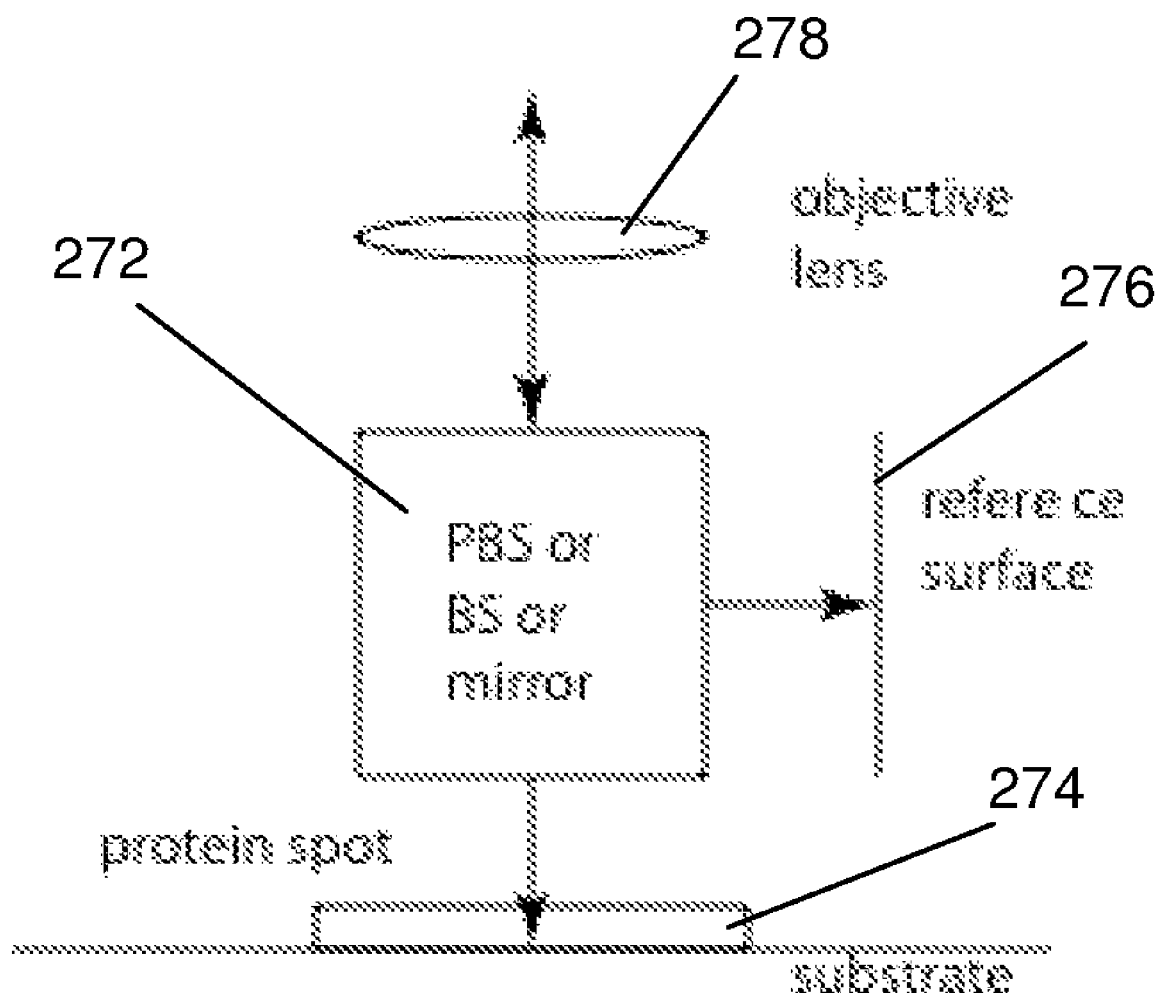
FIG. 17 is a simplified schematic of an embodiment that requires no moving parts by using beam polarization to redirect the illuminating beam back and forth, depending on its vertical and horizontal polarization, either to a protein spot or to a reference surface.

FIG. 17 shows an embodiment that requires no moving parts. This embodiment uses beam polarization control by passing the beam through an electro-optic modulator in a half-wave configuration. The polarization is switched back and forth between orthogonal polarizations. The polarized beam passes through the objective lens 278 and enters the polarizing beam splitter 272 which redirects the illuminating beam back and forth, depending on its vertical and horizontal polarization either to the protein spot 274, or to the reference surface 276. Image acquisition would be synchronized with the polarization.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A molecular interferometric imaging system for detecting an analyte in a sample, the molecular interferometric imaging system comprising:
   an illumination source providing a beam of radiation;
   a pixel array comprising a plurality of pixels for detecting radiation at a plurality of locations in an image plane to produce an image comprising a plurality of pixel readings;
   a biolayer designed to react to the analyte when the biolayer comes in contact with the sample;
   a substrate, the biolayer being located on the substrate, the substrate being designed to convert phase modulation into intensity modulation which can be detected and imaged directly by the pixel array;
   a reference surface;
   an image switching means for switching between a first position in which the beam provided by the illumination source is incident on the biolayer and a reflected sample beam is produced which is directed to the pixel array to generate a sample image, and a second position in which the beam provided by the illumination source is incident on the reference surface and a reflected reference beam is produced which is directed to the pixel array to generate a reference image; and
   a processing means for producing a composite image using the sample image and the reference image for illumination normalization.

2. The system of claim 1, wherein the substrate comprises a support layer and a spacer, the thickness of the spacer being selected to produce an in-line quadrature condition.

3. The system of claim 2, wherein the spacer acts as the reference surface.

4. The system of claim 2, wherein the support layer is silicon and the spacer is a thermal oxide layer.

5. The system of claim 4, wherein the thickness of the oxide layer is 120 nm.

6. The system of claim 1, wherein the substrate acts as the reference surface, and the image switching means is a stage for moving the substrate and the biolayer between the first position and the second position.

7. The system of claim 1, wherein the biolayer comprises a plurality of separate spots deposited on the substrate with the substrate being exposed to separate the plurality of separate spots.

8. The system of claim 7, wherein the substrate acts as the reference surface.

9. The system of claim 1, wherein the processing means computes a difference between the plurality of pixel readings of the reference image and the plurality of pixel readings of the sample image on a pixel by pixel basis.

10. The system of claim 1, wherein the illumination source is a laser tuned to a desired frequency, the desired frequency being selected such that the reflected radiation from the substrate and the radiation from the biolayer are in an in-line quadrature condition.

11. The system of claim 1, further comprising an illumination filter.

12. The system of claim 11, wherein the illumination source produces a multi-frequency beam and the illumination filter filters the beam such that only a desired frequency passes through the illumination filter, the desired frequency being selected such that the reflected radiation from the substrate and the radiation from the biolayer are in an in-line quadrature condition.

13. The system of claim 11, wherein the illumination source produces a multi-frequency beam and the illumination filter filters the beam such that only a first wavelength and a second wavelength pass through the illumination filter, the first and second wavelengths being selected such that the reflected radiation from the substrate and the radiation from the biolayer are in an in-line quadrature condition, the first wavelength being different from the second wavelength.

14. The system of claim 11, further comprising a detection filter, the detection filter being matched to the illumination filter to produce a desired property in the beam incident on the pixel array.

15. The system of claim 1, further comprising a beam splitter, the beam splitter directing the beam from the illumination source to the image plane and directing the reflected beam from the image plane to the pixel array.

16. The system of claim 1, further comprising a trigger to synchronize image collection with switching by the image switching means.

17. The system of claim 16, wherein the image switching means is a mirror that moves between the first position to view the biolayer and the second position to view the reference surface.

18. The system of claim 16, wherein the image switching means is a spinning disc that includes an aperture, the spinning disc being in the first position when the biolayer is visible through the aperture and the spinning disc being in the second position when the biolayer is not visible through the aperture.

19. The system of claim 16, wherein the image switching means is a polarizing beam splitter that switches back and forth between orthogonal polarizations, the polarizing beam splitter being in the first position when the polarization setting directs the beam to the biolayer and the polarizing beam splitter being in the second position when the orthogonal polarization setting directs the beam to the reference surface.

20. The system of claim 1, further comprising a trigger to synchronize image collection with changing of properties of the beam incident on the pixel array.

21. The system of claim 1, wherein the biolayer is immersed in a fluid during collection of the sample image.

22. The system of claim 21, wherein the fluid is actively flowing during collection of the sample image.

23. The system of claim 1, wherein the image switching means is a stage, the stage moving between the first position in which a first set of pixels of the plurality of pixels is exposed to the biolayer, and the second position in which a second set of pixels of the plurality of pixels is exposed to the biolayer, there being no intersection between the first set of pixels and the second set of pixels.

24. A method of molecular interferometric imaging for detecting an analyte in a sample using a pixel array comprising a plurality of pixels for detecting radiation at a plurality of locations in an image plane, and a substrate designed to convert phase modulation into intensity modulation which can be detected and imaged directly by the pixel array, the method comprising:
  exposing a biolayer that is deposited on the substrate to the sample, the biolayer being designed to react to the analyte when the biolayer comes in contact with the sample;
  positioning an image switching means in a first position;
  illuminating the biolayer with a radiation source to produce a sample beam;
  capturing the sample beam in a sample image using the pixel array;
  positioning the image switching means in a second position;
  illuminating a reference surface with the radiation source to produce a reference beam;
  capturing the reference beam in a reference image using the pixel array;
  computing a composite image using the sample image and the reference image for illumination normalization.

25. The method of claim 24 wherein the sample image exposes a first set of pixels to the biolayer and exposes a second set of pixels to the reference surface, and the reference image exposes the first set of pixels to the reference surface and exposes the second set of pixels to the biolayer, and the computing a composite image step comprises:
  subtracting the pixel readings from the sample image from the pixel readings of the reference image.

26. The method of claim 24 wherein the sample image exposes a first set of pixels to the biolayer and exposes a second set of pixels to the reference surface, and the reference image exposes the first set of pixels to the reference surface and exposes the second set of pixels to the biolayer, and the computing a composite image step comprises:
  computing, on a pixel by pixel basis, $$I_{Diff} = 2\frac{(I_A - I_B)}{(I_A + I_B)} \quad (4)$$

where $I_B$ are the pixel readings from the sample image and $I_A$ are the pixel readings from the reference image.

27. The method of claim 24, further comprising filtering the radiation source such that only a desired set of wavelengths are captured in the sample image and the reference image.

28. The method of claim 24, further comprising rotating the image switching means to move between the first position and the second position.

29. The method of claim 24, further comprising synchronizing the capturing of the sample image and the reference image with movement of the image switching means.

30. The method of claim 24, wherein the sample image is collected while the biolayer is immersed in a liquid.

31. The method of claim 30, wherein the sample beam passes through the liquid.

32. The method of claim 30, wherein the sample beam does not pass through the liquid.

33. The method of claim 24, wherein
capturing the sample image comprises capturing a multiple exposure image of the biolayer as it traverses the field of view of the pixel array, and
capturing the reference image comprises capturing a multiple exposure image of the reference surface as it traverses the field of view of the pixel array.

34. The method of claim 24, wherein
capturing the sample image comprises capturing a time lapse image of the biolayer as it traverses the field of view of the pixel array, and
capturing the reference image comprises capturing a time lapse image of the reference surface as it traverses the field of view of the pixel array.

* * * * *